United States Patent
Lee et al.

(10) Patent No.: US 12,370,309 B2
(45) Date of Patent: Jul. 29, 2025

(54) ADAPTIVE UPDATE OF AUTOMATIC INSULIN DELIVERY (AID) CONTROL PARAMETERS

(71) Applicant: Insulet Corporation, Acton, MA (US)

(72) Inventors: Joon Bok Lee, Acton, MA (US); Yibin Zheng, Hartland, WI (US); Jason O'Connor, Acton, MA (US)

(73) Assignee: INSULET CORPORATION, Acton, MA (US)

( * ) Notice: Subject to any disclaimer, the term of this patent is extended or adjusted under 35 U.S.C. 154(b) by 806 days.

(21) Appl. No.: 17/687,808

(22) Filed: Mar. 7, 2022

(65) Prior Publication Data

US 2022/0288311 A1    Sep. 15, 2022

Related U.S. Application Data

(60) Provisional application No. 63/165,252, filed on Mar. 24, 2021, provisional application No. 63/158,918, filed on Mar. 10, 2021.

(51) Int. Cl.
*A61M 5/172*   (2006.01)
*A61B 5/00*    (2006.01)
(Continued)

(52) U.S. Cl.
CPC ....... *A61M 5/1723* (2013.01); *A61B 5/14532* (2013.01); *A61B 5/4839* (2013.01);
(Continued)

(58) Field of Classification Search
None
See application file for complete search history.

(56) References Cited

U.S. PATENT DOCUMENTS

| 303,013 A | 8/1884 | Horton |
|---|---|---|
| 2,797,149 A | 6/1957 | Skeggs |

(Continued)

FOREIGN PATENT DOCUMENTS

| AU | 2015200834 A1 | 3/2015 |
|---|---|---|
| AU | 2015301146 A1 | 3/2017 |

(Continued)

OTHER PUBLICATIONS

US 5,954,699 A, 09/1999, Jost et al. (withdrawn)
(Continued)

*Primary Examiner* — Manuel A Mendez
(74) *Attorney, Agent, or Firm* — GOODWIN PROCTER LLP

(57) ABSTRACT

Exemplary embodiments may modify the cost function parameters based on current and projected mean outcomes in blood glucose level control performance. The exemplary embodiments may modify the weight coefficient R for the insulin cost so that the value of R is not fixed and is not based solely on clinical determined values. Exemplary embodiments may also adjust the cost function to address persistent low-level blood glucose level excursions for users. The exemplary embodiments may reduce the penalty of the insulin cost by the sum of the converted insulin cost of the glucose excursions above target for a period divided by a number of cycles of average insulin action time. The AID system reduces the insulin cost by the lack of insulin in previous cycles.

17 Claims, 8 Drawing Sheets

(51) Int. Cl.
  *A61B 5/145* (2006.01)
  *A61M 5/142* (2006.01)
  *G06Q 30/0283* (2023.01)
  *G16H 20/17* (2018.01)

(52) U.S. Cl.
  CPC ......... *A61M 5/142* (2013.01); *G06Q 30/0283* (2013.01); *G16H 20/17* (2018.01); *A61M 2005/14208* (2013.01); *A61M 2205/52* (2013.01); *A61M 2230/201* (2013.01)

(56) References Cited

U.S. PATENT DOCUMENTS

| | | |
|---|---|---|
| 3,631,847 A | 1/1972 | Hobbs |
| 3,634,039 A | 1/1972 | Brondy |
| 3,812,843 A | 5/1974 | Wootten et al. |
| 3,841,328 A | 10/1974 | Jensen |
| 3,963,380 A | 6/1976 | Thomas, Jr. et al. |
| 4,055,175 A | 10/1977 | Clemens et al. |
| 4,146,029 A | 3/1979 | Ellinwood, Jr. |
| 4,151,845 A | 5/1979 | Clemens |
| 4,245,634 A | 1/1981 | Albisser et al. |
| 4,368,980 A | 1/1983 | Aldred et al. |
| 4,373,527 A | 2/1983 | Fischell |
| 4,403,984 A | 9/1983 | Ash et al. |
| 4,464,170 A | 8/1984 | Clemens et al. |
| 4,469,481 A | 9/1984 | Kobayashi |
| 4,475,901 A | 10/1984 | Kraegen et al. |
| 4,526,568 A | 7/1985 | Clemens et al. |
| 4,526,569 A | 7/1985 | Bernardi |
| 4,529,401 A | 7/1985 | Leslie et al. |
| 4,559,033 A | 12/1985 | Stephen et al. |
| 4,559,037 A | 12/1985 | Franetzki et al. |
| 4,573,968 A | 3/1986 | Parker |
| 4,624,661 A | 11/1986 | Arimond |
| 4,633,878 A | 1/1987 | Bombardieri |
| 4,657,529 A | 4/1987 | Prince et al. |
| 4,685,903 A | 8/1987 | Cable et al. |
| 4,731,726 A | 3/1988 | Allen, III |
| 4,743,243 A | 5/1988 | Vaillancourt |
| 4,755,173 A | 7/1988 | Konopka et al. |
| 4,781,688 A | 11/1988 | Thoma et al. |
| 4,781,693 A | 11/1988 | Martinez et al. |
| 4,808,161 A | 2/1989 | Kamen |
| 4,854,170 A | 8/1989 | Brimhall et al. |
| 4,886,499 A | 12/1989 | Cirelli et al. |
| 4,900,292 A | 2/1990 | Berry et al. |
| 4,919,596 A | 4/1990 | Slate et al. |
| 4,925,444 A | 5/1990 | Orkin et al. |
| 4,940,527 A | 7/1990 | Kazlauskas et al. |
| 4,975,581 A | 12/1990 | Robinson et al. |
| 4,976,720 A | 12/1990 | Machold et al. |
| 4,981,140 A | 1/1991 | Wyatt |
| 4,994,047 A | 2/1991 | Walker et al. |
| 5,007,286 A | 4/1991 | Malcolm et al. |
| 5,097,834 A | 3/1992 | Skrabal |
| 5,102,406 A | 4/1992 | Arnold |
| 5,109,850 A | 5/1992 | Blanco et al. |
| 5,125,415 A | 6/1992 | Bell |
| 5,134,079 A | 7/1992 | Cusack et al. |
| 5,153,827 A | 10/1992 | Coutre et al. |
| 5,165,406 A | 11/1992 | Wong |
| 5,176,662 A | 1/1993 | Bartholomew et al. |
| 5,178,609 A | 1/1993 | Ishikawa |
| 5,207,642 A | 5/1993 | Orkin et al. |
| 5,232,439 A | 8/1993 | Campbell et al. |
| 5,237,993 A | 8/1993 | Skrabal |
| 5,244,463 A | 9/1993 | Cordner, Jr. et al. |
| 5,257,980 A | 11/1993 | Van Antwerp et al. |
| 5,273,517 A | 12/1993 | Barone et al. |
| 5,281,808 A | 1/1994 | Kunkel |
| 5,299,571 A | 4/1994 | Mastrototaro |
| 5,308,982 A | 5/1994 | Ivaldi et al. |
| 5,342,298 A | 8/1994 | Michaels et al. |
| 5,377,674 A | 1/1995 | Kuestner |
| 5,380,665 A | 1/1995 | Cusack et al. |
| 5,385,539 A | 1/1995 | Maynard |
| 5,389,078 A | 2/1995 | Zalesky |
| 5,411,889 A | 5/1995 | Hoots et al. |
| 5,421,812 A | 6/1995 | Langley et al. |
| 5,468,727 A | 11/1995 | Phillips et al. |
| 5,505,709 A | 4/1996 | Funderburk et al. |
| 5,505,828 A | 4/1996 | Wong et al. |
| 5,507,288 A | 4/1996 | Bocker et al. |
| 5,533,389 A | 7/1996 | Kamen et al. |
| 5,558,640 A | 9/1996 | Pfeiler et al. |
| 5,569,186 A | 10/1996 | Lord et al. |
| 5,584,813 A | 12/1996 | Livingston et al. |
| 5,609,572 A | 3/1997 | Lang |
| 5,665,065 A | 9/1997 | Colman et al. |
| 5,678,539 A | 10/1997 | Schubert et al. |
| 5,685,844 A | 11/1997 | Marttila |
| 5,685,859 A | 11/1997 | Kornerup |
| 5,693,018 A | 12/1997 | Kriesel et al. |
| 5,697,899 A | 12/1997 | Hillman et al. |
| 5,700,695 A | 12/1997 | Yassinzadeh et al. |
| 5,703,364 A | 12/1997 | Rosenthal |
| 5,714,123 A | 2/1998 | Sohrab |
| 5,716,343 A | 2/1998 | Kriesel et al. |
| 5,722,397 A | 3/1998 | Eppstein |
| 5,741,228 A | 4/1998 | Lambrecht et al. |
| 5,746,217 A | 5/1998 | Erickson et al. |
| 5,755,682 A | 5/1998 | Knudson et al. |
| 5,758,643 A | 6/1998 | Wong et al. |
| 5,800,405 A | 9/1998 | McPhee |
| 5,800,420 A | 9/1998 | Gross et al. |
| 5,801,057 A | 9/1998 | Smart et al. |
| 5,804,048 A | 9/1998 | Wong et al. |
| 5,817,007 A | 10/1998 | Fodgaard et al. |
| 5,820,622 A | 10/1998 | Gross et al. |
| 5,823,951 A | 10/1998 | Messerschmidt |
| 5,840,020 A | 11/1998 | Heinonen et al. |
| 5,848,991 A | 12/1998 | Gross et al. |
| 5,851,197 A | 12/1998 | Marano et al. |
| 5,858,005 A | 1/1999 | Kriesel |
| 5,865,806 A | 2/1999 | Howell |
| 5,871,470 A | 2/1999 | McWha |
| 5,879,310 A | 3/1999 | Sopp et al. |
| 5,902,253 A | 5/1999 | Pfeiffer et al. |
| 5,931,814 A | 8/1999 | Alex et al. |
| 5,932,175 A | 8/1999 | Knute et al. |
| 5,935,099 A | 8/1999 | Peterson et al. |
| 5,947,911 A | 9/1999 | Wong et al. |
| 5,971,941 A | 10/1999 | Simons et al. |
| 5,993,423 A | 11/1999 | Choi |
| 5,997,501 A | 12/1999 | Gross et al. |
| 6,017,318 A | 1/2000 | Gauthier et al. |
| 6,024,539 A | 2/2000 | Blomquist |
| 6,032,059 A | 2/2000 | Henning et al. |
| 6,036,924 A | 3/2000 | Simons et al. |
| 6,040,578 A | 3/2000 | Malin et al. |
| 6,049,727 A | 4/2000 | Crothall |
| 6,050,978 A | 4/2000 | Orr et al. |
| 6,058,934 A | 5/2000 | Sullivan |
| 6,066,103 A | 5/2000 | Duchon et al. |
| 6,071,292 A | 6/2000 | Makower et al. |
| 6,072,180 A | 6/2000 | Kramer et al. |
| 6,077,055 A | 6/2000 | Vilks |
| 6,090,092 A | 7/2000 | Fowles et al. |
| 6,101,406 A | 8/2000 | Hacker et al. |
| 6,102,872 A | 8/2000 | Doneen et al. |
| 6,115,673 A | 9/2000 | Malin et al. |
| 6,123,827 A | 9/2000 | Wong et al. |
| 6,124,134 A | 9/2000 | Stark |
| 6,126,637 A | 10/2000 | Kriesel et al. |
| 6,128,519 A | 10/2000 | Say |
| 6,142,939 A | 11/2000 | Eppstein et al. |
| 6,143,164 A | 11/2000 | Heller et al. |
| 6,157,041 A | 12/2000 | Thomas et al. |
| 6,161,028 A | 12/2000 | Braig et al. |
| 6,162,639 A | 12/2000 | Douglas |
| 6,196,046 B1 | 3/2001 | Braig et al. |
| 6,200,287 B1 | 3/2001 | Keller et al. |
| 6,200,338 B1 | 3/2001 | Solomon et al. |

(56) References Cited

U.S. PATENT DOCUMENTS

| | | |
|---|---|---|
| 6,214,629 B1 | 4/2001 | Freitag et al. |
| 6,226,082 B1 | 5/2001 | Roe |
| 6,244,776 B1 | 6/2001 | Wiley |
| 6,261,065 B1 | 7/2001 | Nayak et al. |
| 6,262,798 B1 | 7/2001 | Shepherd et al. |
| 6,270,455 B1 | 8/2001 | Brown |
| 6,271,045 B1 | 8/2001 | Douglas et al. |
| 6,280,381 B1 | 8/2001 | Malin et al. |
| 6,285,448 B1 | 9/2001 | Kuenstner |
| 6,309,370 B1 | 10/2001 | Haim et al. |
| 6,312,888 B1 | 11/2001 | Wong et al. |
| 6,334,851 B1 | 1/2002 | Hayes et al. |
| 6,375,627 B1 | 4/2002 | Mauze et al. |
| 6,379,301 B1 | 4/2002 | Worthington et al. |
| 6,402,689 B1 | 6/2002 | Scarantino et al. |
| 6,470,279 B1 | 10/2002 | Samsoondar |
| 6,475,196 B1 | 11/2002 | Vachon |
| 6,477,901 B1 | 11/2002 | Tadigadapa et al. |
| 6,484,044 B1 | 11/2002 | Lilienfeld-Toal |
| 6,491,656 B1 | 12/2002 | Morris |
| 6,512,937 B2 | 1/2003 | Blank et al. |
| 6,525,509 B1 | 2/2003 | Petersson et al. |
| 6,528,809 B1 | 3/2003 | Thomas et al. |
| 6,540,672 B1 | 4/2003 | Simonsen et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,553,841 B1 | 4/2003 | Blouch |
| 6,554,798 B1 | 4/2003 | Mann et al. |
| 6,556,850 B1 | 4/2003 | Braig et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,562,014 B2 | 5/2003 | Lin et al. |
| 6,569,125 B2 | 5/2003 | Jepson et al. |
| 6,572,542 B1 | 6/2003 | Houben et al. |
| 6,572,545 B2 | 6/2003 | Knobbe et al. |
| 6,574,490 B2 | 6/2003 | Abbink et al. |
| 6,575,905 B2 | 6/2003 | Knobbe et al. |
| 6,580,934 B1 | 6/2003 | Braig et al. |
| 6,618,603 B2 | 9/2003 | Varalli et al. |
| 6,633,772 B2 | 10/2003 | Ford et al. |
| 6,645,142 B2 | 11/2003 | Braig et al. |
| 6,653,091 B1 | 11/2003 | Dunn et al. |
| 6,662,030 B2 | 12/2003 | Khalil et al. |
| 6,669,663 B1 | 12/2003 | Thompson |
| 6,678,542 B2 | 1/2004 | Braig et al. |
| 6,699,221 B2 | 3/2004 | Vaillancourt |
| 6,718,189 B2 | 4/2004 | Rohrscheib et al. |
| 6,721,582 B2 | 4/2004 | Trepagnier et al. |
| 6,728,560 B2 | 4/2004 | Kollias et al. |
| 6,740,059 B2 | 5/2004 | Flaherty |
| 6,740,072 B2 | 5/2004 | Starkweather et al. |
| 6,751,490 B2 | 6/2004 | Esenaliev et al. |
| 6,758,835 B2 | 7/2004 | Close et al. |
| 6,780,156 B2 | 8/2004 | Haueter et al. |
| 6,810,290 B2 | 10/2004 | Lebel et al. |
| 6,837,858 B2 | 1/2005 | Cunningham et al. |
| 6,837,988 B2 | 1/2005 | Leong et al. |
| 6,846,288 B2 | 1/2005 | Nagar et al. |
| 6,862,534 B2 | 3/2005 | Sterling et al. |
| 6,865,408 B1 | 3/2005 | Abbink et al. |
| 6,890,291 B2 | 5/2005 | Robinson et al. |
| 6,936,029 B2 | 8/2005 | Mann et al. |
| 6,949,081 B1 | 9/2005 | Chance |
| 6,958,809 B2 | 10/2005 | Sterling et al. |
| 6,989,891 B2 | 1/2006 | Braig et al. |
| 6,990,366 B2 | 1/2006 | Say et al. |
| 7,008,404 B2 | 3/2006 | Nakajima |
| 7,009,180 B2 | 3/2006 | Sterling et al. |
| 7,016,713 B2 | 3/2006 | Gardner et al. |
| 7,018,360 B2 | 3/2006 | Flaherty et al. |
| 7,025,743 B2 | 4/2006 | Mann et al. |
| 7,025,744 B2 | 4/2006 | Utterberg et al. |
| 7,027,848 B2 | 4/2006 | Robinson et al. |
| 7,043,288 B2 | 5/2006 | Davis, III et al. |
| 7,060,059 B2 | 6/2006 | Keith et al. |
| 7,061,593 B2 | 6/2006 | Braig et al. |
| 7,096,124 B2 | 8/2006 | Sterling et al. |
| 7,115,205 B2 | 10/2006 | Robinson et al. |
| 7,128,727 B2 | 10/2006 | Flaherty et al. |
| 7,139,593 B2 | 11/2006 | Kavak et al. |
| 7,139,598 B2 | 11/2006 | Hull et al. |
| 7,144,384 B2 | 12/2006 | Gorman et al. |
| 7,171,252 B1 | 1/2007 | Scarantino et al. |
| 7,190,988 B2 | 3/2007 | Say et al. |
| 7,204,823 B2 | 4/2007 | Estes et al. |
| 7,248,912 B2 | 7/2007 | Gough et al. |
| 7,267,665 B2 | 9/2007 | Steil et al. |
| 7,271,912 B2 | 9/2007 | Sterling et al. |
| 7,278,983 B2 | 10/2007 | Ireland et al. |
| 7,291,107 B2 | 11/2007 | Hellwig et al. |
| 7,291,497 B2 | 11/2007 | Holmes et al. |
| 7,303,549 B2 | 12/2007 | Flaherty et al. |
| 7,303,622 B2 | 12/2007 | Loch et al. |
| 7,303,922 B2 | 12/2007 | Jeng et al. |
| 7,354,420 B2 | 4/2008 | Steil et al. |
| 7,388,202 B2 | 6/2008 | Sterling et al. |
| 7,402,153 B2 | 7/2008 | Steil et al. |
| 7,404,796 B2 | 7/2008 | Ginsberg |
| 7,429,255 B2 | 9/2008 | Thompson |
| 7,460,130 B2 | 12/2008 | Salganicoff |
| 7,481,787 B2 | 1/2009 | Gable et al. |
| 7,491,187 B2 | 2/2009 | Van Den Berghe et al. |
| 7,500,949 B2 | 3/2009 | Gottlieb et al. |
| 7,509,156 B2 | 3/2009 | Flanders |
| 7,547,281 B2 | 6/2009 | Hayes et al. |
| 7,569,030 B2 | 8/2009 | Ebel et al. |
| 7,608,042 B2 | 10/2009 | Goldberger et al. |
| 7,651,845 B2 | 1/2010 | Doyle, III et al. |
| 7,680,529 B2 | 3/2010 | Kroll |
| 7,734,323 B2 | 6/2010 | Blomquist et al. |
| 7,766,829 B2 | 8/2010 | Sloan et al. |
| 7,785,258 B2 | 8/2010 | Braig et al. |
| 7,806,854 B2 | 10/2010 | Damiano et al. |
| 7,806,886 B2 | 10/2010 | Kanderian, Jr. et al. |
| 7,918,825 B2 | 4/2011 | OConnor et al. |
| 7,946,985 B2 | 5/2011 | Mastrototaro et al. |
| 7,972,296 B2 | 7/2011 | Braig et al. |
| 8,221,345 B2 | 7/2012 | Blomquist |
| 8,251,907 B2 | 8/2012 | Sterling et al. |
| 8,449,524 B2 | 5/2013 | Braig et al. |
| 8,452,359 B2 | 5/2013 | Rebec et al. |
| 8,454,576 B2 | 6/2013 | Mastrototaro et al. |
| 8,467,980 B2 | 6/2013 | Campbell et al. |
| 8,478,557 B2 | 7/2013 | Hayter et al. |
| 8,547,239 B2 | 10/2013 | Peatfield et al. |
| 8,597,274 B2 | 12/2013 | Sloan et al. |
| 8,622,988 B2 | 1/2014 | Hayter |
| 8,810,394 B2 | 8/2014 | Kalpin |
| 9,061,097 B2 | 6/2015 | Holt et al. |
| 9,171,343 B1 | 10/2015 | Fischell et al. |
| 9,233,204 B2 | 1/2016 | Booth et al. |
| 9,486,571 B2 | 11/2016 | Rosinko |
| 9,579,456 B2 | 2/2017 | Budiman et al. |
| 9,743,224 B2 | 8/2017 | San Vicente et al. |
| 9,907,515 B2 | 3/2018 | Doyle, III et al. |
| 9,980,140 B1 | 5/2018 | Spencer et al. |
| 9,984,773 B2 | 5/2018 | Gondhalekar et al. |
| 10,248,839 B2 | 4/2019 | Levy et al. |
| 10,335,464 B1 | 7/2019 | Michelich et al. |
| 10,583,250 B2 | 3/2020 | Mazlish et al. |
| 10,737,024 B2 | 8/2020 | Schmid |
| 10,987,468 B2 | 4/2021 | Mazlish et al. |
| 11,197,964 B2 | 12/2021 | Sjolund et al. |
| 11,260,169 B2 | 3/2022 | Estes |
| 2001/0021803 A1 | 9/2001 | Blank et al. |
| 2001/0034023 A1 | 10/2001 | Stanton, Jr. et al. |
| 2001/0034502 A1 | 10/2001 | Moberg et al. |
| 2001/0051377 A1 | 12/2001 | Hammer et al. |
| 2001/0053895 A1 | 12/2001 | Vaillancourt |
| 2002/0010401 A1 | 1/2002 | Bushmakin et al. |
| 2002/0010423 A1 | 1/2002 | Gross et al. |

(56) References Cited

U.S. PATENT DOCUMENTS

| | | |
|---|---|---|
| 2002/0016568 A1 | 2/2002 | Lebel et al. |
| 2002/0040208 A1 | 4/2002 | Flaherty et al. |
| 2002/0123740 A1 | 9/2002 | Flaherty et al. |
| 2002/0128543 A1 | 9/2002 | Leonhardt |
| 2002/0147423 A1 | 10/2002 | Burbank et al. |
| 2002/0155425 A1 | 10/2002 | Han et al. |
| 2002/0161288 A1 | 10/2002 | Shin et al. |
| 2003/0023148 A1 | 1/2003 | Lorenz et al. |
| 2003/0050621 A1 | 3/2003 | Lebel et al. |
| 2003/0060692 A1 | 3/2003 | Ruchti et al. |
| 2003/0086074 A1 | 5/2003 | Braig et al. |
| 2003/0086075 A1 | 5/2003 | Braig et al. |
| 2003/0090649 A1 | 5/2003 | Sterling et al. |
| 2003/0100040 A1 | 5/2003 | Bonnecaze et al. |
| 2003/0130616 A1 | 7/2003 | Steil et al. |
| 2003/0135388 A1 | 7/2003 | Martucci et al. |
| 2003/0144582 A1 | 7/2003 | Cohen et al. |
| 2003/0163097 A1 | 8/2003 | Fleury et al. |
| 2003/0195404 A1 | 10/2003 | Knobbe et al. |
| 2003/0208113 A1 | 11/2003 | Mault et al. |
| 2003/0208154 A1 | 11/2003 | Close et al. |
| 2003/0212379 A1 | 11/2003 | Bylund et al. |
| 2003/0216627 A1 | 11/2003 | Lorenz et al. |
| 2003/0220605 A1 | 11/2003 | Bowman, Jr. et al. |
| 2004/0010207 A1 | 1/2004 | Flaherty et al. |
| 2004/0034295 A1 | 2/2004 | Salganicoff |
| 2004/0045879 A1 | 3/2004 | Shults et al. |
| 2004/0051368 A1 | 3/2004 | Caputo et al. |
| 2004/0064259 A1 | 4/2004 | Haaland et al. |
| 2004/0097796 A1 | 5/2004 | Berman et al. |
| 2004/0116847 A1 | 6/2004 | Wall |
| 2004/0122353 A1 | 6/2004 | Shahmirian et al. |
| 2004/0133166 A1 | 7/2004 | Moberg et al. |
| 2004/0147034 A1 | 7/2004 | Gore et al. |
| 2004/0171983 A1 | 9/2004 | Sparks et al. |
| 2004/0203357 A1 | 10/2004 | Nassimi |
| 2004/0204868 A1 | 10/2004 | Maynard et al. |
| 2004/0215492 A1 | 10/2004 | Choi |
| 2004/0220517 A1 | 11/2004 | Starkweather et al. |
| 2004/0241736 A1 | 12/2004 | Hendee et al. |
| 2004/0249308 A1 | 12/2004 | Forssell |
| 2005/0003470 A1 | 1/2005 | Nelson et al. |
| 2005/0020980 A1 | 1/2005 | Noue et al. |
| 2005/0022274 A1 | 1/2005 | Campbell et al. |
| 2005/0033148 A1 | 2/2005 | Haueter et al. |
| 2005/0049179 A1 | 3/2005 | Davidson et al. |
| 2005/0065464 A1 | 3/2005 | Talbot et al. |
| 2005/0065465 A1 | 3/2005 | Lebel et al. |
| 2005/0075624 A1 | 4/2005 | Miesel |
| 2005/0105095 A1 | 5/2005 | Pesach et al. |
| 2005/0137573 A1 | 6/2005 | McLaughlin |
| 2005/0171503 A1 | 8/2005 | Van Den Berghe et al. |
| 2005/0182306 A1 | 8/2005 | Sloan |
| 2005/0192494 A1 | 9/2005 | Ginsberg |
| 2005/0192557 A1 | 9/2005 | Brauker et al. |
| 2005/0197621 A1 | 9/2005 | Poulsen et al. |
| 2005/0203360 A1 | 9/2005 | Brauker et al. |
| 2005/0203461 A1 | 9/2005 | Flaherty et al. |
| 2005/0238507 A1 | 10/2005 | Dilanni et al. |
| 2005/0261660 A1 | 11/2005 | Choi |
| 2005/0272640 A1 | 12/2005 | Doyle, III et al. |
| 2005/0277912 A1 | 12/2005 | John |
| 2006/0009727 A1 | 1/2006 | OMahony et al. |
| 2006/0079809 A1 | 4/2006 | Goldberger et al. |
| 2006/0100494 A1 | 5/2006 | Kroll |
| 2006/0134323 A1 | 6/2006 | OBrien |
| 2006/0167350 A1 | 7/2006 | Monfre et al. |
| 2006/0173406 A1 | 8/2006 | Hayes et al. |
| 2006/0189925 A1 | 8/2006 | Gable et al. |
| 2006/0189926 A1 | 8/2006 | Hall et al. |
| 2006/0197015 A1 | 9/2006 | Sterling et al. |
| 2006/0200070 A1 | 9/2006 | Callicoat et al. |
| 2006/0204535 A1 | 9/2006 | Johnson |
| 2006/0229531 A1 | 10/2006 | Goldberger et al. |
| 2006/0253085 A1 | 11/2006 | Geismar et al. |
| 2006/0264895 A1 | 11/2006 | Flanders |
| 2006/0270983 A1 | 11/2006 | Lord et al. |
| 2006/0276771 A1 | 12/2006 | Galley et al. |
| 2006/0282290 A1 | 12/2006 | Flaherty et al. |
| 2007/0016127 A1 | 1/2007 | Staib et al. |
| 2007/0060796 A1 | 3/2007 | Kim |
| 2007/0060869 A1 | 3/2007 | Tolle et al. |
| 2007/0060872 A1 | 3/2007 | Hall et al. |
| 2007/0083160 A1 | 4/2007 | Hall et al. |
| 2007/0106135 A1 | 5/2007 | Sloan et al. |
| 2007/0116601 A1 | 5/2007 | Patton |
| 2007/0118405 A1 | 5/2007 | Campbell et al. |
| 2007/0129690 A1 | 6/2007 | Rosenblatt et al. |
| 2007/0142720 A1 | 6/2007 | Ridder et al. |
| 2007/0173761 A1 | 7/2007 | Kanderian et al. |
| 2007/0173974 A1 | 7/2007 | Lin et al. |
| 2007/0179352 A1 | 8/2007 | Randlov et al. |
| 2007/0191716 A1 | 8/2007 | Goldberger et al. |
| 2007/0197163 A1 | 8/2007 | Robertson |
| 2007/0225675 A1 | 9/2007 | Robinson et al. |
| 2007/0244381 A1 | 10/2007 | Robinson et al. |
| 2007/0249007 A1 | 10/2007 | Rosero |
| 2007/0264707 A1 | 11/2007 | Liederman et al. |
| 2007/0282269 A1 | 12/2007 | Carter et al. |
| 2007/0287985 A1 | 12/2007 | Estes et al. |
| 2007/0293843 A1 | 12/2007 | Ireland et al. |
| 2008/0033272 A1 | 2/2008 | Gough et al. |
| 2008/0051764 A1 | 2/2008 | Dent et al. |
| 2008/0058625 A1 | 3/2008 | McGarraugh et al. |
| 2008/0065050 A1 | 3/2008 | Sparks et al. |
| 2008/0071157 A1 | 3/2008 | McGarraugh et al. |
| 2008/0071158 A1 | 3/2008 | McGarraugh et al. |
| 2008/0078400 A1 | 4/2008 | Martens et al. |
| 2008/0097289 A1 | 4/2008 | Steil et al. |
| 2008/0132880 A1 | 6/2008 | Buchman |
| 2008/0161664 A1 | 7/2008 | Mastrototaro et al. |
| 2008/0172026 A1 | 7/2008 | Blomquist |
| 2008/0177165 A1 | 7/2008 | Blomquist et al. |
| 2008/0188796 A1 | 8/2008 | Steil et al. |
| 2008/0200838 A1 | 8/2008 | Goldberger et al. |
| 2008/0206067 A1 | 8/2008 | De Corral et al. |
| 2008/0208113 A1 | 8/2008 | Damiano et al. |
| 2008/0214919 A1 | 9/2008 | Harmon et al. |
| 2008/0228056 A1 | 9/2008 | Blomquist et al. |
| 2008/0249386 A1 | 10/2008 | Besterman et al. |
| 2008/0269585 A1 | 10/2008 | Ginsberg |
| 2008/0269714 A1 | 10/2008 | Mastrototaro et al. |
| 2008/0269723 A1 | 10/2008 | Mastrototaro et al. |
| 2008/0287906 A1 | 11/2008 | Burkholz et al. |
| 2009/0006061 A1 | 1/2009 | Thukral et al. |
| 2009/0018406 A1 | 1/2009 | Yodfat et al. |
| 2009/0030398 A1 | 1/2009 | Yodfat et al. |
| 2009/0036753 A1 | 2/2009 | King |
| 2009/0043240 A1 | 2/2009 | Robinson et al. |
| 2009/0054753 A1 | 2/2009 | Robinson et al. |
| 2009/0069743 A1 | 3/2009 | Krishnamoorthy et al. |
| 2009/0069745 A1 | 3/2009 | Estes et al. |
| 2009/0069787 A1 | 3/2009 | Estes et al. |
| 2009/0099521 A1 | 4/2009 | Gravesen et al. |
| 2009/0105573 A1 | 4/2009 | Malecha |
| 2009/0131861 A1 | 5/2009 | Braig et al. |
| 2009/0156922 A1 | 6/2009 | Goldberger et al. |
| 2009/0156924 A1 | 6/2009 | Shariati et al. |
| 2009/0163781 A1 | 6/2009 | Say et al. |
| 2009/0198350 A1 | 8/2009 | Thiele |
| 2009/0221890 A1 | 9/2009 | Saffer et al. |
| 2009/0228214 A1 | 9/2009 | Say et al. |
| 2009/0318791 A1 | 12/2009 | Kaastrup |
| 2009/0326343 A1 | 12/2009 | Gable et al. |
| 2010/0057042 A1 | 3/2010 | Hayter |
| 2010/0114026 A1 | 5/2010 | Karratt et al. |
| 2010/0121170 A1 | 5/2010 | Rule |
| 2010/0137784 A1 | 6/2010 | Cefai et al. |
| 2010/0152658 A1 | 6/2010 | Hanson et al. |
| 2010/0174228 A1 | 7/2010 | Buckingham et al. |
| 2010/0211003 A1 | 8/2010 | Sundar et al. |
| 2010/0228110 A1 | 9/2010 | Tsoukalis |
| 2010/0262117 A1 | 10/2010 | Magni et al. |
| 2010/0262434 A1 | 10/2010 | Shaya |

(56) References Cited

U.S. PATENT DOCUMENTS

| | | |
|---|---|---|
| 2010/0295686 A1 | 11/2010 | Sloan et al. |
| 2010/0298765 A1 | 11/2010 | Budiman et al. |
| 2011/0021584 A1 | 1/2011 | Berggren et al. |
| 2011/0028817 A1 | 2/2011 | Jin et al. |
| 2011/0054390 A1 | 3/2011 | Searle et al. |
| 2011/0054399 A1 | 3/2011 | Chong et al. |
| 2011/0124996 A1 | 5/2011 | Reinke et al. |
| 2011/0144586 A1 | 6/2011 | Michaud et al. |
| 2011/0160652 A1 | 6/2011 | Yodfat et al. |
| 2011/0178472 A1 | 7/2011 | Cabiri |
| 2011/0190694 A1 | 8/2011 | Anier, Jr. et al. |
| 2011/0202005 A1 | 8/2011 | Yodfat et al. |
| 2011/0218495 A1 | 9/2011 | Remde |
| 2011/0230833 A1 | 9/2011 | Andman et al. |
| 2011/0251509 A1 | 10/2011 | Beyhan et al. |
| 2011/0313680 A1 | 12/2011 | Doyle et al. |
| 2011/0316562 A1 | 12/2011 | Cefai et al. |
| 2012/0003935 A1 | 1/2012 | Lydon et al. |
| 2012/0010594 A1 | 1/2012 | Holt et al. |
| 2012/0030393 A1 | 2/2012 | Ganesh et al. |
| 2012/0053556 A1 | 3/2012 | Lee |
| 2012/0078067 A1 | 3/2012 | Kovatchev et al. |
| 2012/0078161 A1 | 3/2012 | Masterson et al. |
| 2012/0078181 A1 | 3/2012 | Smith et al. |
| 2012/0101451 A1 | 4/2012 | Boit et al. |
| 2012/0123234 A1 | 5/2012 | Atlas et al. |
| 2012/0136336 A1 | 5/2012 | Mastrototaro et al. |
| 2012/0190955 A1 | 7/2012 | Rao et al. |
| 2012/0203085 A1 | 8/2012 | Rebec |
| 2012/0203178 A1 | 8/2012 | Tverskoy |
| 2012/0215087 A1 | 8/2012 | Cobelli et al. |
| 2012/0225134 A1 | 9/2012 | Komorowski |
| 2012/0226259 A1 | 9/2012 | Yodfat et al. |
| 2012/0232520 A1 | 9/2012 | Sloan et al. |
| 2012/0238851 A1 | 9/2012 | Kamen et al. |
| 2012/0271655 A1 | 10/2012 | Knobel et al. |
| 2012/0277668 A1 | 11/2012 | Chawla |
| 2012/0282111 A1 | 11/2012 | Nip et al. |
| 2012/0295550 A1 | 11/2012 | Wilson et al. |
| 2013/0030358 A1 | 1/2013 | Yodfat et al. |
| 2013/0158503 A1 | 6/2013 | Kanderian, Jr. et al. |
| 2013/0178791 A1 | 7/2013 | Javitt |
| 2013/0231642 A1 | 9/2013 | Doyle et al. |
| 2013/0253472 A1 | 9/2013 | Cabiri |
| 2013/0261406 A1 | 10/2013 | Rebec et al. |
| 2013/0296823 A1 | 11/2013 | Melker et al. |
| 2013/0317753 A1 | 11/2013 | Kamen et al. |
| 2013/0338576 A1 | 12/2013 | OConnor et al. |
| 2014/0005633 A1 | 1/2014 | Finan |
| 2014/0200426 A1 | 1/2014 | Taub et al. |
| 2014/0066886 A1 | 3/2014 | Roy et al. |
| 2014/0074033 A1 | 3/2014 | Sonderegger et al. |
| 2014/0121635 A1 | 5/2014 | Hayter |
| 2014/0128839 A1 | 5/2014 | Dilanni et al. |
| 2014/0135880 A1 | 5/2014 | Baumgartner et al. |
| 2014/0146202 A1 | 5/2014 | Boss et al. |
| 2014/0180203 A1 | 6/2014 | Budiman et al. |
| 2014/0180240 A1 | 6/2014 | Finan et al. |
| 2014/0200559 A1 | 7/2014 | Doyle et al. |
| 2014/0230021 A1 | 8/2014 | Birthwhistle et al. |
| 2014/0276554 A1* | 9/2014 | Finan .............. A61M 5/14244 604/504 |
| 2014/0276556 A1 | 9/2014 | Saint et al. |
| 2014/0278123 A1 | 9/2014 | Prodhom et al. |
| 2014/0309615 A1 | 10/2014 | Mazlish |
| 2014/0316379 A1 | 10/2014 | Sonderegger et al. |
| 2014/0325065 A1 | 10/2014 | Birtwhistle et al. |
| 2015/0018633 A1 | 1/2015 | Kovachev et al. |
| 2015/0025329 A1 | 1/2015 | Amarasingham et al. |
| 2015/0025495 A1 | 1/2015 | Peyser |
| 2015/0120317 A1 | 4/2015 | Mayou et al. |
| 2015/0134265 A1 | 5/2015 | Kohlbrecher et al. |
| 2015/0165119 A1 | 6/2015 | Palerm et al. |
| 2015/0173674 A1 | 6/2015 | Hayes et al. |
| 2015/0213217 A1 | 7/2015 | Amarasingham et al. |
| 2015/0217052 A1 | 8/2015 | Keenan et al. |
| 2015/0217053 A1 | 8/2015 | Booth et al. |
| 2015/0265767 A1 | 9/2015 | Vazquez et al. |
| 2015/0306314 A1 | 10/2015 | Doyle et al. |
| 2015/0351671 A1 | 12/2015 | Vanslyke et al. |
| 2015/0366945 A1 | 12/2015 | Greene |
| 2016/0015891 A1 | 1/2016 | Papiorek |
| 2016/0038673 A1 | 2/2016 | Morales |
| 2016/0038689 A1 | 2/2016 | Lee et al. |
| 2016/0051749 A1 | 2/2016 | Istoc |
| 2016/0082187 A1 | 3/2016 | Schaible et al. |
| 2016/0089494 A1 | 3/2016 | Guerrini |
| 2016/0175520 A1 | 6/2016 | Palerm et al. |
| 2016/0228641 A1 | 8/2016 | Gescheit et al. |
| 2016/0243318 A1 | 8/2016 | Despa et al. |
| 2016/0256087 A1 | 9/2016 | Doyle et al. |
| 2016/0287512 A1 | 10/2016 | Cooper et al. |
| 2016/0302054 A1 | 10/2016 | Kimura et al. |
| 2016/0331310 A1 | 11/2016 | Kovatchev |
| 2016/0354543 A1 | 12/2016 | Cinar et al. |
| 2017/0049386 A1 | 2/2017 | Abraham et al. |
| 2017/0143899 A1 | 5/2017 | Gondhalekar et al. |
| 2017/0143900 A1 | 5/2017 | Rioux et al. |
| 2017/0156682 A1 | 6/2017 | Doyle et al. |
| 2017/0173261 A1 | 6/2017 | OConnor et al. |
| 2017/0189625 A1 | 7/2017 | Cirillo et al. |
| 2017/0281877 A1 | 10/2017 | Marlin et al. |
| 2017/0296746 A1 | 10/2017 | Chen et al. |
| 2017/0311903 A1 | 11/2017 | Davis et al. |
| 2017/0348482 A1 | 12/2017 | Duke et al. |
| 2018/0036495 A1 | 2/2018 | Searle et al. |
| 2018/0040255 A1 | 2/2018 | Freeman et al. |
| 2018/0075200 A1 | 3/2018 | Davis et al. |
| 2018/0075201 A1 | 3/2018 | Davis et al. |
| 2018/0075202 A1 | 3/2018 | Davis et al. |
| 2018/0092576 A1 | 4/2018 | O'Connor et al. |
| 2018/0126073 A1 | 5/2018 | Wu et al. |
| 2018/0169334 A1 | 6/2018 | Grosman et al. |
| 2018/0200434 A1 | 7/2018 | Mazlish et al. |
| 2018/0200438 A1 | 7/2018 | Mazlish et al. |
| 2018/0200441 A1 | 7/2018 | Desborough et al. |
| 2018/0204636 A1 | 7/2018 | Edwards et al. |
| 2018/0277253 A1 | 9/2018 | Gondhalekar et al. |
| 2018/0289891 A1 | 10/2018 | Finan et al. |
| 2018/0296757 A1 | 10/2018 | Finan et al. |
| 2018/0342317 A1 | 11/2018 | Skirble et al. |
| 2018/0369479 A1 | 12/2018 | Hayter et al. |
| 2019/0076600 A1 | 3/2019 | Grosman et al. |
| 2019/0240403 A1 | 8/2019 | Palerm et al. |
| 2019/0290844 A1 | 9/2019 | Monirabbasi et al. |
| 2019/0336683 A1 | 11/2019 | O'Connor et al. |
| 2019/0336684 A1 | 11/2019 | O'Connor et al. |
| 2019/0348157 A1 | 11/2019 | Booth et al. |
| 2020/0046268 A1 | 2/2020 | Patek et al. |
| 2020/0101222 A1 | 4/2020 | Lintereur et al. |
| 2020/0101223 A1 | 4/2020 | Lintereur et al. |
| 2020/0101225 A1 | 4/2020 | O'Connor et al. |
| 2020/0219625 A1 | 7/2020 | Kahlbaugh |
| 2020/0342974 A1 | 10/2020 | Chen et al. |
| 2021/0050085 A1 | 2/2021 | Hayter et al. |
| 2021/0098105 A1 | 4/2021 | Lee et al. |
| 2022/0023536 A1 | 1/2022 | Graham et al. |

FOREIGN PATENT DOCUMENTS

| | | |
|---|---|---|
| CN | 1297140 A | 5/2001 |
| DE | 19756872 A1 | 7/1999 |
| EP | 0341049 A2 | 11/1989 |
| EP | 0496305 A2 | 7/1992 |
| EP | 0549341 A1 | 6/1993 |
| EP | 1491144 A1 | 12/2004 |
| EP | 0801578 B1 | 7/2006 |
| EP | 2139382 A1 | 1/2010 |
| EP | 2397181 A1 | 12/2011 |
| EP | 2666520 A1 | 11/2013 |
| EP | 2695573 A2 | 2/2014 |
| EP | 2830499 A1 | 2/2015 |
| EP | 2943149 A1 | 11/2015 |
| EP | 3177344 A1 | 6/2017 |

(56) References Cited

FOREIGN PATENT DOCUMENTS

| | | |
|---|---|---|
| EP | 3314548 A1 | 5/2018 |
| EP | 1571582 B1 | 4/2019 |
| EP | 2897071 B1 | 5/2019 |
| EP | 3607985 A1 | 2/2020 |
| GB | 2443261 A | 4/2008 |
| JP | 51125993 A | 11/1976 |
| JP | 02131777 A | 5/1990 |
| JP | 2004283378 A | 10/2007 |
| JP | 2017525451 A | 9/2017 |
| JP | 2018153569 A | 10/2018 |
| JP | 2019525276 A | 9/2019 |
| TW | 200740148 A | 10/2007 |
| TW | M452390 U | 5/2013 |
| WO | 9800193 A1 | 1/1998 |
| WO | 9956803 A1 | 11/1999 |
| WO | 0030705 A1 | 6/2000 |
| WO | 200032258 A1 | 6/2000 |
| WO | 0172354 A2 | 10/2001 |
| WO | 2002015954 A1 | 2/2002 |
| WO | 2002043866 A2 | 6/2002 |
| WO | 2002082990 A1 | 10/2002 |
| WO | 2003016882 A1 | 2/2003 |
| WO | 2003039362 A1 | 5/2003 |
| WO | 2003045233 A1 | 6/2003 |
| WO | 2004043250 A1 | 5/2004 |
| WO | 2005110601 A1 | 5/2004 |
| WO | 2004092715 A1 | 10/2004 |
| WO | 2005051170 A2 | 6/2005 |
| WO | 2005082436 A1 | 9/2005 |
| WO | 2005113036 A1 | 12/2005 |
| WO | 2006053007 A2 | 5/2006 |
| WO | 2007064835 A2 | 6/2007 |
| WO | 2007078937 A1 | 7/2007 |
| WO | 2008024810 A2 | 2/2008 |
| WO | 2008029403 A1 | 3/2008 |
| WO | 2008133702 A1 | 11/2008 |
| WO | 2009045462 A1 | 4/2009 |
| WO | 2009049252 A1 | 4/2009 |
| WO | 2009066287 A3 | 5/2009 |
| WO | 2009066288 A1 | 5/2009 |
| WO | 2009098648 A2 | 8/2009 |
| WO | 2009134380 A2 | 11/2009 |
| WO | 2010053702 A1 | 5/2010 |
| WO | 2010132077 A1 | 11/2010 |
| WO | 2010138848 A1 | 12/2010 |
| WO | 2010147659 A2 | 12/2010 |
| WO | 2011095483 A1 | 8/2011 |
| WO | 2012045667 A2 | 4/2012 |
| WO | 2012108959 A1 | 8/2012 |
| WO | 2012134588 A1 | 10/2012 |
| WO | 2012177353 A1 | 12/2012 |
| WO | 2012178134 A2 | 12/2012 |
| WO | 2013078200 A1 | 5/2013 |
| WO | 2013134486 A2 | 9/2013 |
| WO | 20130149186 A1 | 10/2013 |
| WO | 2013177565 A1 | 11/2013 |
| WO | 2013182321 A1 | 12/2013 |
| WO | 2014109898 A1 | 7/2014 |
| WO | 2014110538 A1 | 7/2014 |
| WO | 2014194183 A2 | 12/2014 |
| WO | 2015056259 A1 | 4/2015 |
| WO | 2015061493 A1 | 4/2015 |
| WO | 2015073211 A1 | 5/2015 |
| WO | 2015081337 A2 | 6/2015 |
| WO | 2015187366 A1 | 12/2015 |
| WO | 2016004088 A1 | 1/2016 |
| WO | 2016022650 A1 | 2/2016 |
| WO | 2016041873 A1 | 3/2016 |
| WO | 2016089702 A1 | 6/2016 |
| WO | 2016141082 A1 | 9/2016 |
| WO | 2016161254 A1 | 10/2016 |
| WO | 2017004278 A1 | 1/2017 |
| WO | 2017091624 A1 | 6/2017 |
| WO | 2017105600 A1 | 6/2017 |
| WO | 2017184988 A1 | 10/2017 |
| WO | 2017205816 A1 | 11/2017 |
| WO | 2018009614 A1 | 1/2018 |
| WO | 2018067748 A1 | 4/2018 |
| WO | 2018120104 A1 | 7/2018 |
| WO | 2018136799 A1 | 7/2018 |
| WO | WO-2018204568 A1 * 11/2018 ......... A61B 5/14503 |
| WO | 2019077482 A1 | 4/2019 |
| WO | 2019094440 A1 | 5/2019 |
| WO | 2019213493 A1 | 11/2019 |
| WO | 2019246381 A1 | 12/2019 |
| WO | 2020081393 A1 | 4/2020 |
| WO | 2021011738 A1 | 1/2021 |

OTHER PUBLICATIONS

Anonymous: "Artificial pancreas—Wikipedia", Mar. 13, 2018 (Mar. 13, 2018), XP055603712, Retrieved from the Internet: URL: https://en.wikipedia.org/wiki/Artificial_pancreas [retrieved on Jul. 9, 2019] section "Medical Equipment" and the figure labeled "The medical equipment approach to an artifical pancreas".

Kaveh et al., "Blood Glucose Regulation via Double Loop Higher Order Sliding Mode Control and Multiple Sampling Rate." Paper presented at the proceedings of the 17th IFAC World Congress, Seoul, Korea (Jul. 2008).

Dassau et al., "Real-Time Hypoglycemia Prediction Suite Using Contineous Glucose Monitoring," Diabetes Care, vol. 33, No. 6, 1249-1254 (2010).

International Search Report and Written Opinion for International Patent Application No. PCT/US17/53262, mailed on Dec. 13, 2017, 8 pages.

Van Heusden et al., "Control-Relevant Models for Glucose Control using A Priori Patient Characteristics", IEEE Transactions on Biomedical Engineering, vol. 59, No. 7, (Jul. 1, 2012) pp. 1839-1849.

Doyle III et al., "Run-to-Run Control Strategy for Diabetes Management." Paper presented at 23rd Annual International Conference of the IEEE Engineering in Medicine and Biology Society, Istanbul, Turkey. (Oct. 2001).

Bequette, B.W., and Desemone, J., "Intelligent Dosing Systems": Need for Design and Analysis Based on Control Theory, Diabetes Technology and Therapeutics 9(6): 868-873 (2004).

Parker et al., "A Model-Based Agorithm for Blood Gucose Control in Type 1 Diabetic Patients." IEEE Transactions on Biomedical Engineering, 46 (2) 148-147 (1999).

International Search Report and Written Opinion for International Patent Application No. PCT/US2017/015601, mailed May 16, 2017, 12 pages.

International Search Report and Written Opinion for the International Patent Application No. PCT/US2018/018901, mailed on Aug. 6, 2018, 12 pages.

International Search Report and Written Opinion for International Patent Application No. PCT/US2018/052467, mailed Jan. 4, 2019, 13 pages.

"How to Create a QR Code that Deep Links to Your Mobile App", Pure Oxygen Labs, web<https://pureoxygenlabs.com/how-to-create-a-qr-codes-that-deep-link-to-your-mobile-app/>. Year:2017.

"Read NFC Tags with an iPHone App on iOS 11", GoToTags, Sep. 11, 2017, web <https://gototags.com/blog/read-hfc-tags-with-an-iphone-app-on-ios-11/>. (Year:2017).

International Search Report and Written Opinion for International Patent Application No. PCT/US2016/063350, mailed on Mar. 27, 2017, 9 pages.

Extended Search Report mailed Aug. 13, 2018, issued in European Patent Application No. 16753053.4, 9 pages.

International Search Report and Written Opinion for International Patent Application No. PCT/US16/18452, mailed on Apr. 29, 2015, 9 pages.

International Preliminary Report on Patentability mailed Aug. 31, 2017, issued in PCT Patent Application No. PCT/US2016/018452, 7 pages.

International Search Report and Written Opinion for International Patent Application No. PCT/US2019/055862, mailed on Mar. 11, 2020.

(56) References Cited

OTHER PUBLICATIONS

International Search Report and Written Opinion for Application No. PCT/US2019/030562, Sep. 25, 2019, 19 pages.
International Search Report and Written Opinion for the International Patent Application No. PCT/US2020/052125, mailed Aug. 12, 2020, 15 pages.
International Search Report and Written Opinion for the International Patent Application No. PCT/US2020/050332, mailed Sep. 12, 2020, 12 pages.
European Patent Office, "Notification of Transmittal of the ISR and the Written Opinion of the International Searching Authority, or the Declaration," in PCT Application No. PCT/GB2015/050248, Jun. 23, 2015, 12 pages.
International Search Report and Written Opinion for the International Patent Application No. PCT/US2021/012246, mailed Apr. 13, 2021, 15 pages.
International Search Report and Written Opinion for the International Patent Application No. PCT/US2021/013639, mailed Apr. 28, 2021, 14 pages.
International Search Report and Written Opinion for the International Patent Application No. PCT/US2020/063326, mailed May 3, 2021, 17 pages.
European Search Report for the European Patent Application. No. 21168591, mailed Oct. 13, 2021, 4 pages.
International Search Report and Written Opinion for the International Patent Application No. PCT/US2021/041954, mailed Oct. 25, 2021, 13 pages.
International Search Report and Written Opinion for the International Patent Application No. PCT/US2021/022694, mailed Jun. 25, 2021, 13 pages.
International Search Report and Written Opinion for the International Patent Application No. PCT/US2021/017664, mailed May 26, 2021, 16 pages.
International Search Report and Written Opinion for the International Patent Application No. PCT/US2022/012896, mailed Apr. 22, 2022, 15 pages.
International Search Report and Written Opinion for the International Patent Application No. PCT/US2022/013470, mailed May 6, 2022, 14 pages.
International Search Report and Written Opinion for the International Patent Application No. PCT/US2022/013473, mailed May 6, 2022, 13 pages.
International Search Report and Written Opinion for the International Patent Application No. PCT/US2022/019079, mailed Jun. 2, 2022, 14 pages.
International Search Report and Written Opinion for the International Patent Application No. PCT/US2022/018453, mailed Jun. 2, 2022, 13 pages.
International Search Report and Written Opinion for the International Patent Application No. PCT/US22/018700, mailed Jun. 7, 2022, 13 pages.
International Search Report and Written Opinion for the International Patent Application No. PCT/US22/019080, mailed Jun. 7, 2022, 14 pages.
International Search Report and Written Opinion for the International Patent Application No. PCT/US22/019664, mailed Jun. 7, 2022, 14 pages.
International Search Report and Written Opinion for International Patent Application No. PCT/US2021/051027, mailed on Jan. 7, 2022, 16 pages.
International Search Report and Written Opinion for International Patent Application No. PCT/US2021/052372, mailed Jan. 26, 2022, 15 pages.
International Search Report and Written Opinion for the International Patent Application No. PCT/US2021/046607, mailed Jan. 31, 2022, 20 pages.
International Search Report and Written Opinion for the International Patent Application No. PCT/US2021/055745, mailed Feb. 14, 2022, 13 pages.
International Search Report and Written Opinion for the International Patent Application No. PCT/US21/060618, mailed Mar. 21, 2022, 15 pages.
Herrero Pau et al: "Enhancing automatic closed-loop glucose control in type 1 diabetes with an adaptive meal bolus calculator—in silicoevaluation under intra-day variability", Computer Methods and Programs in Biomedicine, Elsevier, Amsterdam, NL, vol. 146, Jun. 1, 2017 (Jun. 1, 2017), pp. 125-131, XP085115607, ISSN: 0169-2607, DOI:10.1016/J.CMPB.2017.05.010.
Marie Aude Qemerais: "Preliminary Evaluation of a New Semi-Closed-Loop Insulin Therapy System over the prandial period in Adult Patients with type I diabetes: the WP6. 0 Diabeloop Study", Journal of Diabetes Science and Technology Diabetes Technology Society Reprints and permissions, Jan. 1, 2014, pp. 1177-1184, Retrieved from the Internet: URL:http://journals.sagepub.com/doi/pdf/10.1177/1932296814545668 [retrieved on Jun. 6, 2022] chapter "Functioning of the Algorithm" chapter "Statistical Analysis" p. 1183, left-hand column, line 16-line 23.
Anonymous: "Kernel density estimation", Wikipedia, Nov. 13, 2020 (Nov. 13, 2020), pp. 1-12, XP055895569, Retrieved from the Internet: URL:https://en.wikipedia.org/w/index.php?title=Kernel_density_estimation&oldid=988508333 [retrieved on Jun. 6, 2022].
Anonymous: "openaps / oref0 /lib/determine-basal-js", openaps repository, Nov. 9, 2019 (Nov. 9, 2019), pp. 1-17, XP055900283, Retrieved from the Internet: URL:https://github.com/openaps/oref0/blob/master/lib/determine-basal/determine-basal.js [retrieved on Jun. 6, 2022] line 116-line 118, line 439-line 446.
Anonymous: "AndroidAPS screens", AndroidAPS documentation, Oct. 4, 2020 (Oct. 4, 2020), pp. 1-12, XP055894824, Retrieved from the Internet: URL:https://github.com/openaps/AndroidAPSdocs/blob/25d8acf8b28262b411b34f416f173ac0814d7e14/docs/EN/Getting-Started/Screenshots.md [retrieved on Jun. 6, 2022].
Kozak Milos et al: "Issue #2473 of AndroidAPS", MilosKozak / AndroidAPS Public repository, Mar. 4, 2020 (Mar. 4, 2020), pp. 1-4, XP055900328, Retrieved from the Internet: URL:https://github.com/MilosKozak/AndroidAPS/issues/2473 [retrieved on Jun. 6, 2022].
International Search Report and Written Opinion for the International Patent Application No. PCT/US2021/052855, mailed Dec. 22, 2021, 11 pages.
International Search Report and Written Opinion for the International Patent Application No. PCT/US2021/047771, mailed Dec. 22, 2021, 11 pages.
Medication Bar Code System Implementation Planning Section I: A Bar Code Primer for Leaders, Aug. 2013.
Medication Bar Code System Implementation Planning Section II: Building the Case for Automated Identification of Medications, Aug. 2013.
Villareal et al. (2009) in: Distr. Comp. Art. Intell. Bioninf. Soft Comp. Amb. Ass. Living; Int. Work Conf. Art. Neural Networks (IWANN) 2009, Lect. Notes Comp. Sci. vol. 5518; S. Omatu et al. (Eds.), pp. 870-877.
Fox, Ian G.; Machine Learning for Physiological Time Series: Representing and Controlling Blood Glucose for Diabetes Management; University of Michigan. ProQuest Dissertations Publishing, 2020. 28240142. (Year: 2020).
Unger, Jeff, et al., "Glucose Control in the Hospitalized Patient," Emerg. Med 36(9):12-18 (2004).
"Glucommander FAQ" downloaded from https://adaendo.com/GlucommanderFAQ.html on Mar. 16, 2009.
Finfer, Simon & Heritier, Stephane. (2009). The NICE-SUGAR (Normoglycaemia in Intensive Care Evaluation and Survival Using Glucose Algorithm Regulation) Study: statistical analysis plan. Critical care and resuscitation : journal of the Australasian Academy of Critical Care Medicine. 11. 46-57.
Letters to the Editor regarding "Glucose Control in Critically Ill Patients," N Engl J Med 361: 1, Jul. 2, 2009.
"Medtronic is Leading a Highly Attractive Growth Market," Jun. 2, 2009.
Davidson, Paul C., et al. "Glucommander: An Adaptive, Computer-Directed System for IV Insulin Shown to be Safe, Simple, and Effective in 120,618 Hours of Operation," Atlanta Diabetes Associates presentation.

(56) References Cited

OTHER PUBLICATIONS

Davidson, Paul C., et al. "Pumpmaster and Glucommander," presented at the MiniMed Symposium, Atlanta GA, Dec. 13, 2003.
Kanji S., et al. "Reliability of point-of-care testing for glucose measurement in critically ill adults," Critical Care Med, vol. 33, No. 12, pp. 2778-2785, 2005.
Krinsley James S., "Severe hypoglycemia in critically ill patients: Risk factors and outcomes," Critical Care Med, vol. 35, No. 10, pp. 1-6, 2007.
International Search Report and Written Opinion for the International Patent Application No. PCT/US2021/016283, mailed Jun. 2, 2021, 15 pages.
Farkas et al. "Single-Versus Triple-Lumen Central Catheter-Related Sepsis: A Prospective Randomized Study in a Critically Ill Population" The American Journal of Medicine, Sep. 1992, vol. 93, p. 277-282.
Davidson, Paul C., et al., A computer-directed intravenous insulin system shown to be safe, simple, and effective in 120,618 h of operation, Diabetes Care, vol. 28, No. 10, Oct. 2005, pp. 2418-2423.
R Anthony Shaw, et al., "Infrared Spectroscopy in Clinical and Dianostic Analysis," Encyclopedia of Analytical Chemistry, ed. Robert A. Meyers, John Wiley & Sons, Ltd., pp. 1-20, 2006.
Gorke, A "Microbial Contamination Of Haemodialysis Catheter Connections" Journal of Renal Care, European Dialysis & Transplant Nurses Association.
Lovich et al. "Central venous catheter infusions: A laboratory model shows large differences in drug delivery dynamics related to catheter dead volume" Critical Care Med 2007 vol. 35, No. 12.
Van Den Berghe, Greet, M.D., Ph.D., et al., Intensive Insulin Therapy in Critically Ill Patients, The New England Journal of Medicine, vol. 345, No. 19, Nov. 8, 2001, pp. 1359-1367.
Schlegel et al, "Multilumen Central Venous Catheters Increase Risk for Catheter-Related Bloodstream Infection: Prospective Surveillance Study" Infection 2008; 36: 322-327.
Wilson, George S., et al., Progress toward the Development of an Implantable Sensor for Glucose, Clin. Chem., vol. 38, No. 9, 1992, pp. 1613-1617.
Yeung et al. "Infection Rate for Single Lumen v Triple Lumen Subclavian Catheters" Infection Control and Hospital Epidemiology, vol. 9, No. 4 (Apr. 1988) pp. 154-158 The University of Chicago Press.
International Search Report and Written Opinion, International Application No. PCT/US2010/033794 mailed Jul. 16, 2010 (OPTIS. 247VPC).
International Search Report and Written Opinion in PCT/US2008/079641 (Optis.203VPC) dated Feb. 25, 2009.
Berger, "Measurement of Analytes in Human Serum and Whole Blood Samples by Near-Infrared Raman Spectroscopy," Ph.D. Thesis, Massachusetts Institute of Technology, Chapter 4, pp. 50-73,1998.
Berger, "An Enhanced Algorithm for Linear Multivariate Calibration," Analytical Chemistry, vol. 70, No. 3, pp. 623-627, Feb. 1, 1998.
Billman et. al., "Clinical Performance of an In line Ex-Vivo Point of Care Monitor: A Multicenter Study," Clinical Chemistry 48: 11, pp. 2030-2043, 2002.
Widness et al., "Clinical Performance on an In-Line Point-of-Care Monitor in Neonates"; Pediatrics, vol. 106, No. 3, pp. 497-504, Sep. 2000.
Finkielman et al., "Agreement Between Bedside Blood and Plasma Glucose Measurement in the ICU Setting"; retrieved from http://www.chestjournal.org; CHEST/127/5/May 2005.
Glucon Critical Care Blood Glucose Monitor; Glucon; retrieved from http://www.glucon.com.
Fogt, et al., "Development and Evaluation of a Glucose Analyzer for a Glucose-Controlled Insulin Infusion System (Biostator)"; Clinical Chemistry, vol. 24, No. 8, pp. 1366-1372, 1978.
Vonach et al., "Application of Mid-Infrared Transmission Spectrometry to the Direct Determination of Glucose in Whole Blood," Applied Spectroscopy, vol. 52, No. 6, 1998, pp. 820-822.
Muniyappa et al., "Current Approaches for assessing insulin sensitivity and resistance in vivo: advantages, limitations, and appropriate usage," AJP-Endocrinol Metab, vol. 294, E15-E26, first published Oct. 23, 2007.
International Preliminary Report on Patentability for the International Patent Application No. PCT/US2019/053603, mailed Apr. 8, 2021, 9 pages.
International Search Report and Written Opinion for the International Patent Application No. PCT/US2019/053603, mailed Jan. 7, 2020, 16 pages.
Dassau et al., "Detection of a meal using continuous glucose monitoring: Implications for an artificial [beta]-cell." Diabetes Care, American Diabetes Association, Alexandria, VA, US, 31(2):295-300 (2008).
Cameron et al., "Probabilistic Evolving Meal Detection and Estimation of Meal Total Glucose Appearance Author Affiliations", J Diabetes Sci and Tech,vol. Diabetes Technology Society ;(5):1022-1030 (2009).
Lee et al., "A closed-loop artificial pancreas based on model predictive control: Human-friendly identification and automatic meal disturbance rejection", Biomedical Signal Processing and Control, Elsevier, Amsterdam, NL, 4 (4):1746-8094 (2009).
Anonymous: "Fuzzy control system", Wikipedia, Jan. 10, 2020. URL: https://en.wikipedia.org/w/index.php?title=Fuzzy_control_system&oldid=935091190.
An Emilia Fushimi: "Artificial Pancreas: Evaluating the ARG Algorithm Without Meal Annoucement", Journal of Diabetes Science and Technology Diabetes Technology Society, Mar. 22, 2019, pp. 1025-1043.
International Search Report and Written Opinion for the InternationalPatent Application No. PCT/US2021/017441, mailed May 25, 2021, 12 pages.
Mirko Messori et al: "Individualized model predictive control for the artificial pancreas: In silico evaluation of closed-loop glucose control", IEEE Control Systems, vol. 38, No. 1, Feb. 1, 2018, pp. 86-104.
International Search Report and Written Opinion for the International Patent Application No. PCT/US2021/017662, mailed May 26, 2021, 14 pages.
Anonymous: "Reservoir Best Practice and Top Tips" Feb. 7, 2016, URL: https://www.medtronic-diabetes.co.uk/blog/reservoir-best-practice-and-top-tips, p. 1.
Gildon Bradford: "InPen Smart Insulin Pen System: Product Review and User Experience" Diabetes Spectrum, vol. 31, No. 4, Nov. 15, 2018, pp. 354-358.
International Search Report and Written Opinion for the International Patent Application No. PCT/US2021/016050, mailed May 27, 2021, 16 pages.
International Search Report and Written Opinion for the International Patent Application No. PCT/US2020/065226, mailed May 31, 2021, 18 pages.
International Search Report and Written Opinion for the International Patent Application No. PCT/US2021/017659, mailed May 31, 2021, 13 pages.
Montaser Eslam et al., "Seasonal Local Models for Glucose Prediction in Type 1 Diabetes", IEE Journal of Biomedical and Health Informatics, IEEE, Piscataway, NJ, USA, vol. 24, No. 7, Nov. 29, 2019, pp. 2064-2072.
Samadi Sediqeh et al., "Automatic Detection and Estimation of Unannouced Meals for Multivariable Artificial Pancreas System", Diabetis Technology & Therapeutics, vol. 20m No. 3, Mar. 1, 2018, pp. 235-246.
Samadi Sediqeh et al., "Meal Detection and Carbohydrate Estimation Using Continuous Glucose Sensor Data" IEEE Journal of Biomedical and Health Informatics, IEEE, Piscataway, NJ, USA, vol. 21, No. 3, May 1, 2017, pp. 619-627.
Khodaei et al., "Physiological Closed-Loop Contol (PCLC) Systems: Review of a Modern Frontier in Automation", IEEE Access, IEEE, USA, vol. 8, Jan. 20, 2020, pp. 23965-24005.

(56) References Cited

OTHER PUBLICATIONS

E. Atlas et al., "MD-Logic Artificial Pancreas System: A pilot study in adults with type 1 diabetes", Diabetes Care, vol. 33, No. 5, Feb. 11, 2010, pp. 1071-1076.

* cited by examiner

ADAPTIVE UPDATE OF AUTOMATIC INSULIN DELIVERY (AID) CONTROL PARAMETERS

RELATED APPLICATIONS

This application claims the benefit of U.S. Provisional Patent Application No. 63/158,918, filed Mar. 10, 2021, and U.S. Provisional Patent Application No. 63/165,252, filed Mar. 24, 2021, the contents of which are incorporated herein by reference in their entirety.

BACKGROUND

Automatic Insulin Delivery (AID) systems automatically deliver insulin to a user via a delivery mechanism, like an insulin pump. AID systems typically deliver basal insulin to a user, while the user can manually deliver insulin boluses as needed and/or can prompt the insulin pump to deliver insulin boluses as needed. Traditionally, basal insulin accounts for about half of the insulin delivered to a user per day.

AID systems may include a closed control loop that seeks to keep the user's blood glucose level close to a target blood glucose level. In a typical AID system, a controller receives a current blood glucose level reading and compares the current blood glucose level to the target blood glucose level and adjusts the basal insulin delivery to attempt to reduce the difference between the target blood glucose level and the current blood glucose level. In some AID systems, a Model Predictive Control (MPC) approach is adopted. In determining the adjusted basal dosage amount, the controller of the AID system may use a cost function to select the adjusted dosage amount. Specifically, the controller may apply the cost function for a number of possible dosage amounts and select the lowest cost dosage as the adjusted dosage. In other words, the controller seeks to optimize by choosing the lowest cost dosage option.

In one common formulation of the cost function, the cost function is the sum of a weighted glucose cost and a weighted insulin cost. The glucose cost represents the difference between the projected trajectory of the user's blood glucose level over an interval should the adjusted basal amount be chosen for delivery given their current blood glucose level and the target blood glucose level. The glucose cost penalizes positive blood glucose level excursions from the target blood glucose level. The insulin cost represents the difference between the projected insulin trajectory interval over a period should the adjusted basal amount be chosen for delivery and the ideal basal insulin dosage. The insulin cost penalizes insulin excursions above the ideal basal dosage.

The weights of the glucose cost and the insulin cost are determined by weight coefficients $Q$ and $R$. $Q$ is the weight coefficient for the glucose cost, and $R$ is the weight coefficient for insulin cost. The ratio of $Q$ to $R$ is a key parameter for determining the aggressiveness of adaptation such that blood glucose level excursions will be weighed more heavily than insulin excursions. These weight coefficients $Q$ and $R$ conventionally are fixed based on clinical parameters for the user. Thus, the insulin delivery of the AID system will not vary for a fixed set of clinical parameters for the user. As a result, clinical parameters must change for the AID system to improve the control performance at a given blood glucose level. This is problematic in that the AID system may, as a result, not be performing well and does not adjust the control parameters to perform better.

Given the cost function formulation and weight coefficients, conventional AID systems tend to respond conservatively to persistent but small ("low-level") blood glucose level excursions that are slightly above the target blood glucose level. These low-level blood glucose level excursions contribute little to the cost function and as a result, have little effect in increasing the insulin delivered to eliminate or reduce such blood glucose level excursions. This conservative response is intentional for multiple reasons. First, blood glucose level readings may be inaccurate, and the AID system does not want to respond too aggressively to such inaccurate readings. Second, the risk of hypoglycemia is viewed as more worrisome than the risk of hyperglycemia, so the response is biased towards being conservative so as to reduce the risk of delivering too much insulin and driving the user into hypoglycemia. Thus, conventional AID systems are biased against over delivery of insulin.

This conservative approach may be problematic. Persistent low magnitude glucose excursions are not desirable. Such excursions may have negative health consequences for users.

SUMMARY

In accordance with a first inventive aspect, a device for controlling insulin deliveries to a user by an insulin pump includes a glucose sensor interface with a glucose sensor to obtain glucose readings for the user from the glucose sensor and an insulin pump interface for communicating with the insulin pump to control delivery of insulin to the user by the insulin pump. The device further includes a processor configured to implement a control loop to control the delivery of insulin by the insulin pump. The processor selects an insulin delivery dosage for a next delivery among the delivery dosage options that has a best cost function value. The cost function for each of the delivery dosage options has a glucose cost component reflective of a difference between a glucose level that the delivery dosage option is predicted to produce for the user and a projected glucose level with basal insulin delivery. The cost function also has an insulin cost component reflective of a difference between a deviation of the delivery dosage option from a current basal insulin dosage and a converted amount of insulin needed to compensate for glucose excursions above a target for an interval of time. The cost function has a glucose cost weight coefficient for weighting the glucose cost component and has an insulin cost weight coefficient for weighting the insulin cost component.

The device for controlling insulin deliveries may be a drug delivery device that includes the insulin pump. The device for controlling insulin deliveries may be a management device for the insulin pump that does not include the insulin pump. The processor may be configured to calculate the converted amount of insulin needed to compensate for glucose excursions above the target for the interval of time by determining a magnitude of the glucose excursions above the target for the interval. The processor may be configured to determine the magnitude of the glucose excursions above the target for interval by summing glucose excursions above a target of blood glucose level for each cycle in the interval. The processor may be configured for determining the converted amount of insulin needed to compensate for glucose excursions above the target for the interval by applying a conversion factor to the determined magnitude of the glucose excursions above the target.

In accordance with another inventive aspect, a device for controlling insulin deliveries to a user by an insulin pump includes a glucose sensor interface with a glucose sensor to obtain glucose readings for the user from the glucose sensor and an insulin pump interface for communicating with the insulin pump to control delivery of insulin to the user by the insulin pump. The device also includes one or more processors configured to implement a control loop to control the delivery of insulin by the insulin pump such that the processor selects an insulin delivery dosage for a next delivery among the delivery dosage options that has a best cost function value, and the processor also is configured to implement a parallel integral control approach that requests an additional insulin dosage from the insulin pump to eliminate positive glucose excursions that are not eliminated by the control loop.

The one or more processors may be configured so that the parallel integral approach does not request insulin when there are not positive glucose excursions to be eliminated. The device for controlling insulin deliveries may be one of an insulin delivery device or a management device for the for controlling an insulin delivery device. The one or more processors may be configured so that the parallel integral approach determines an amount of insulin needed to eliminate a current magnitude of a positive glucose excursion. The one or more processors may be configured so that the parallel integral approach determines an aggregate magnitude of glucose excursions for a past number of cycles. Further, the one or more processors may be configured so that the parallel integral approach determines a product of the aggregate magnitude of glucose excursions for a past number of cycles and a tuning factor, and the one or more processors may be configured so that the parallel integral approach selects either the amount of insulin needed to eliminate a current magnitude of a positive glucose excursion or the product as the additional insulin dosage.

In accordance with an additional inventive aspect, a device for controlling insulin deliveries to a user by an insulin pump includes a glucose sensor interface with a glucose sensor to obtain glucose readings for the user from the glucose sensor and an insulin pump interface for communicating with the insulin pump to control delivery of insulin to the user by the insulin pump. The device further includes a processor configured to implement a control loop to control the delivery of insulin by the insulin pump. The processor selects an insulin delivery dosage for a next delivery among the delivery dosage options that has a best cost function value. The cost function for each of the delivery dosage options has a glucose cost component reflective of a difference between a glucose level that the delivery dosage option is predicted to produce for the user and a target glucose level for the user. The cost function also has an insulin cost component reflective of a deviation of the delivery dosage option from a current basal insulin dosage. The cost function includes a glucose cost weight coefficient for weighting the glucose cost component and an insulin cost weight coefficient for weighting the insulin cost component. The insulin cost weight coefficient is based on a ratio of time in a desired range for glucose values of the user and a maximum time in the desired range from a history of glucose values for the user.

The insulin cost weight coefficient may also be based on a base value for the insulin cost weight coefficient. The maximum time in the desired range may be a percentage value. The processor may be configured to determine the maximum time in the desired range based on an average target blood glucose value of the user over the history of glucose values for the user. The processor may be configured to determine the maximum time in the desired range based additionally on a percentage of time that glucose values for the user were in range over the history of glucose values for the user. The device for controlling insulin deliveries may be one of an insulin delivery device or a management device for an insulin delivery device. The insulin cost weight coefficient may increase in value as the ratio of time in a desired range for glucose values of the user and maximum time in the desired range from a history of glucose values for the user increases.

DETAILED DESCRIPTION

Exemplary embodiments may address the above-described problems of conventional AID systems. Exemplary embodiments may modify the cost function parameters based on current and projected mean outcomes in blood glucose level control performance. For instance, the exemplary embodiments may modify the weight coefficient R for the insulin cost so that the value of R is not fixed and is not based solely on clinically determined values. The modification may be bounded by the known impacts of the maximum impact of modifying the user's personal therapy parameters. This allows for more customized and better control of blood glucose levels for users. Specifically, if it is determined that the AID system is controlling the blood glucose level of the user well, the cost function is adjusted to be less aggressive (i.e., adapts more slowly), whereas if it is determined that the AID system is controlling the blood glucose level of the user poorly, the cost function is adjusted to be more aggressive (i.e., adapts more quickly). The AID system looks at recent blood glucose level outcomes for the user and the best-case outcome to determine how the AID system is performing in blood glucose level control.

Exemplary embodiments may also adjust the cost function to address persistent low-level blood glucose level excursions for users. The exemplary embodiments may reduce the penalty of the insulin cost by the sum of the converted insulin cost of the glucose excursions above target for a period divided by a number of cycles of average insulin action time. The AID system reduces the insulin cost by the lack of insulin in previous cycles. As a result, the persistent low-level glucose excursions are more likely to be addressed by the AID system.

Figure 1:
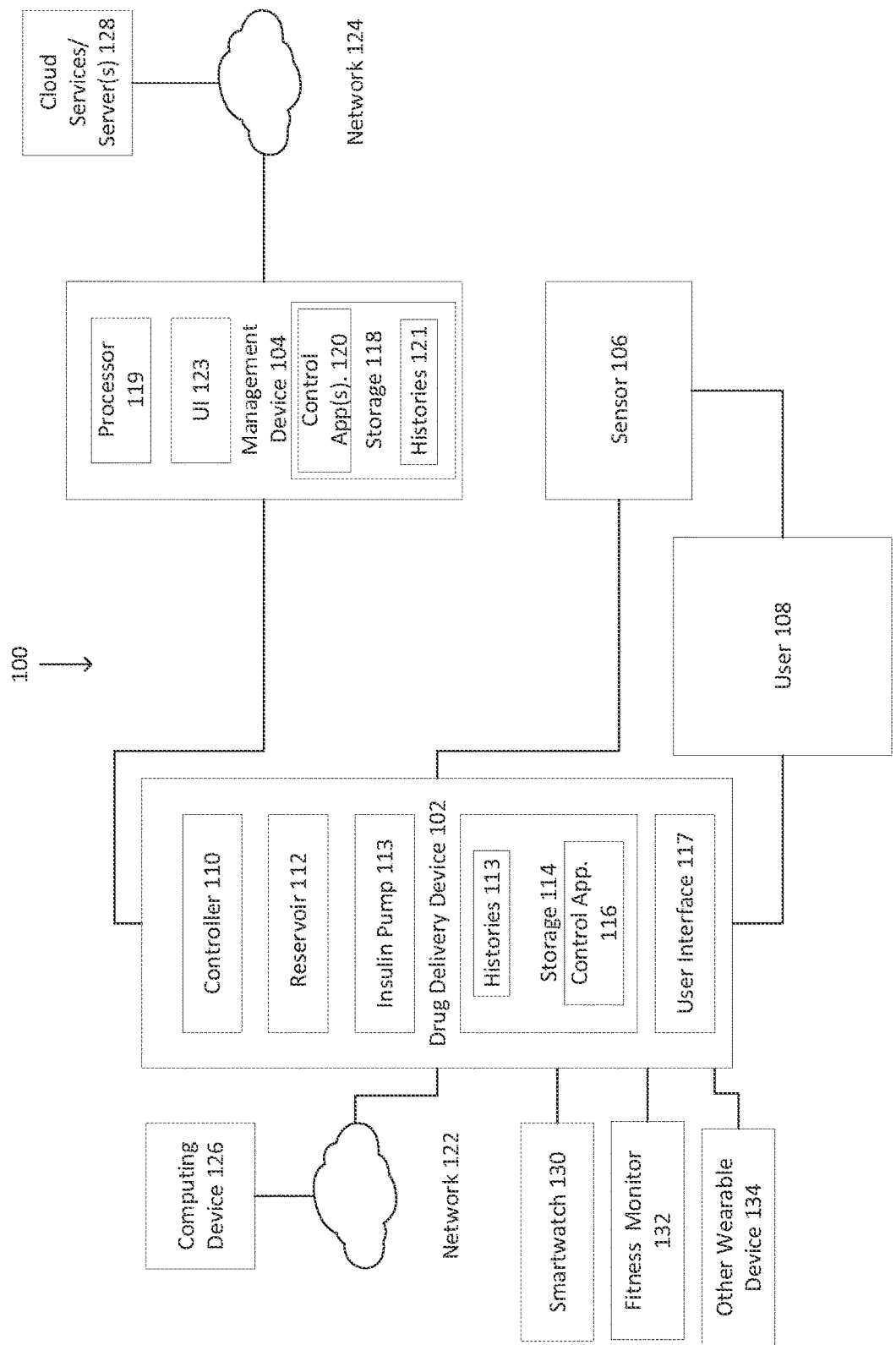
FIG. 1 depicts an illustrative drug delivery system that is suitable for delivering insulin to a user in accordance with exemplary embodiments.

FIG. 1 depicts an illustrative drug delivery system 100 that is suitable for delivering insulin to a user 108 in accordance with exemplary embodiments. The drug delivery system 100 includes a drug delivery device 102. The drug delivery device 102 may be a wearable device that is worn on the body of the user 108. The drug delivery device 102 may be directly coupled to a user (e.g., directly attached to a body part and/or skin of the user 108 via an adhesive or the like). In an example, a surface of the drug delivery device 102 may include an adhesive to facilitate attachment to the user 108.

The drug delivery device 102 may include a controller 110. The controller 110 may be implemented in hardware, software, or any combination thereof. The controller 110 may, for example, be a microprocessor, a logic circuit, a field programmable gate array (FPGA), an application specific integrated circuit (ASIC) or a microcontroller coupled to a memory. The controller 110 may maintain a date and time as well as other functions (e.g., calculations or the like). The controller 110 may be operable to execute a control application 116 stored in the storage 114 that enables the controller 110 to direct operation of the drug delivery device 102. The control application 116 may control insulin delivery to the user 108 per an AID control approach as describe herein. The storage 114 may hold histories 113 for a user, such as a history of automated insulin deliveries, a history of bolus insulin deliveries, meal event history, exercise event history and the like. In addition, the controller 110 may be operable to receive data or information. The storage 114 may include both primary memory and secondary memory. The storage may include random access memory (RAM), read only memory (ROM), optical storage, magnetic storage, removable storage media, solid state storage or the like.

The drug delivery device 102 may include a reservoir 112 for storing insulin for delivery to the user 108 as warranted. A fluid path to the user 108 may be provided, and the drug delivery device 102 may expel the insulin from the reservoir 112 to deliver the insulin to the user 108 via the fluid path. The fluid path may, for example, include tubing coupling the drug delivery device 102 to the user 108 (e.g., tubing coupling a cannula to the reservoir 112).

There may be one or more communications links with one or more devices physically separated from the drug delivery device 102 including, for example, a management device 104 of the user and/or a caregiver of the user and/or a sensor 106. The communication links may include any wired or wireless communication link operating according to any known communications protocol or standard, such as Bluetooth®, Wi-Fi, a near-field communication standard, a cellular standard, or any other wireless protocol The drug delivery device 102 may also include a user interface 117, such as an integrated display device for displaying information to the user 108 and in some embodiments, receiving information from the user 108. The user interface 117 may include a touchscreen and/or one or more input devices, such as buttons, knob or a keyboard.

The drug delivery device 102 may interface with a network 122. The network 122 may include a local area network (LAN), a wide area network (WAN) or a combination therein. A computing device 126 may be interfaced with the network, and the computing device may communicate with the insulin delivery device 102.

The drug delivery system 100 may include a sensor 106 for sensing the levels of one or more analytes. The sensor 106 may be coupled to the user 108 by, for example, adhesive or the like and may provide information or data on one or more medical conditions and/or physical attributes of the user 108. The sensor 106 may, in some exemplary embodiments provide periodic blood glucose concentration measurements and may be a continuous glucose monitor (CGM), or another type of device or sensor that provides blood glucose measurements. The sensor 106 may be physically separate from the drug delivery device 102 or may be an integrated component thereof. The sensor 106 may provide the controller 110 with data indicative of measured or detected blood glucose levels of the user 108. The information or data provided by the sensor 106 may be used to adjust drug delivery operations of the drug delivery device 102.

The drug delivery system 100 may also include the management device 104. In some embodiments, no management device is needed. The management device 104 may be a special purpose device, such as a dedicated personal diabetes manager (PDM) device. The management device 104 may be a programmed general-purpose device, such as any portable electronic device including, for example, a dedicated controller, such as processor, a micro-controller or the like. The management device 104 may be used to program or adjust operation of the drug delivery device 102 and/or the sensor 104. The management device 104 may be any portable electronic device including, for example, a dedicated device, a smartphone, a smartwatch or a tablet. In the depicted example, the management device 104 may include a processor 119 and a storage 118. The processor 119 may execute processes to manage a user's blood glucose levels and for control the delivery of the drug or therapeutic agent to the user 108. The processor 119 may also be operable to execute programming code stored in the storage 118. For example, the storage may be operable to store one or more control applications 120 for execution by the processor 119. The one or more control applications 120 may be responsible for controlling the drug delivery device 102, including the AID delivery of insulin to the user 108. The storage 118 may store the one or more control applications 120, histories 121 like those described above for the insulin delivery device 102 and other data and/or programs.

The management device 104 may include a user interface (UI) 123 for communicating with the user 108. The user interface 123 may include a display, such as a touchscreen, for displaying information. The touchscreen may also be used to receive input when it is a touch screen. The user interface 123 may also include input elements, such as a keyboard, button, knob or the like.

The management device 104 may interface with a network 124, such as a LAN or WAN or combination of such networks. The management device 104 may communicate over network 124 with one or more servers or cloud services 128.

Other devices, like smartwatch 130, fitness monitor 132 and wearable device 134 may be part of the drug delivery system 100. These devices may communicate with the drug delivery device 102 to receive information and/or issue commands to the drug delivery device 102. These devices 130, 132 and 134 may execute computer programming instructions to perform some of the control functions otherwise performed by controller 110 or processor 119. These devices 130, 132 and 134 may include displays for displaying information such as current blood glucose level, insulin on board, insulin deliver history, etc. The display may show a user interface for providing input, such as request a change in basal insulin dosage or delivery of a bolus of insulin. These devices 130, 132 and 134 may also have wireless communication connections with the sensor 106 to directly receive blood glucose level data.

Figure 2:
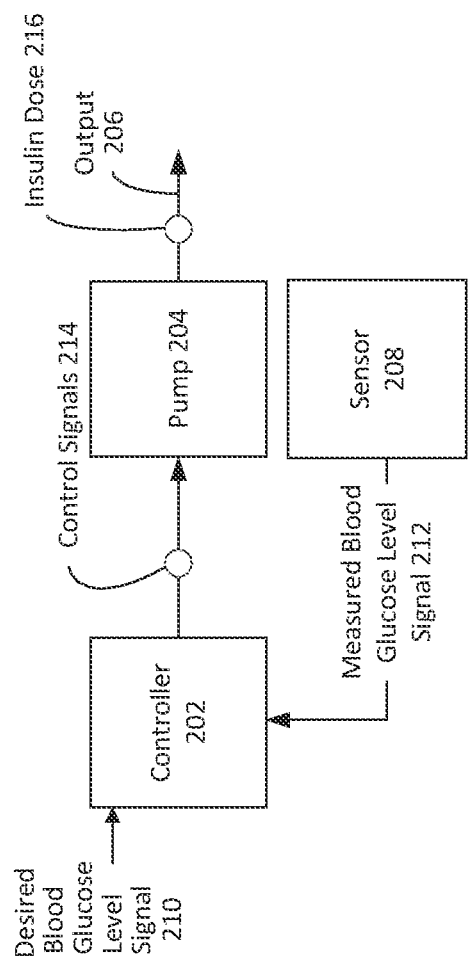
FIG. 2 illustrates a simplified block diagram of an example of a control loop suitable for exemplary embodiments.

As was mentioned above, a control loop may be provided to adjust the basal delivery dosage based on current blood glucose level readings. FIG. 2 illustrates a simplified block diagram of an example of such a control loop 200 suitable for practicing an exemplary embodiment. The example control loop 200 may include a controller 202, a pump mechanism or other fluid extraction mechanism 204 (hereinafter "pump 204"), and a sensor 208. The controller 202, pump 204, and sensor 208 may be communicatively coupled to one another via a wired or wireless communication paths. The sensor 208 may be a glucose monitor such as, for example, a continuous glucose monitor (CGM) 208. The CGM 208 may, for example, be operable to measure blood glucose values of a user to generate the measured actual blood glucose level signal 212.

As shown in the example, the controller 202 may receive a desired blood glucose level signal 210, which may be a first signal, indicating a desired blood glucose level or range for a user. The desired blood glucose level signal 210 may be received from a user interface to the controller or other device, or by an algorithm that automatically determines a desired blood glucose level for a user. The sensor 208 may be coupled to the user and be operable to measure an approximate value of an actual blood glucose level of the user. The measured blood glucose value, the actual blood glucose level, the approximate measured value of the actual blood glucose level are only approximate values of a user's blood glucose level, and it should be understood that there may be errors in the measured blood glucose levels. The errors may, for example, be attributable to a number of factors such as age of the sensor 208, location of the sensor 208 on a body of a user, environmental factors (e.g., altitude, humidity, barometric pressure), or the like. The terms measured blood glucose value, actual blood glucose level, approximate measured value of the actual blood glucose level may be used interchangeably throughout the specification and drawings. In response to the measured blood glucose level or value, the sensor 208 generate a signal indicating the measured blood glucose value. As shown in the example, the controller 202 may also receive from the sensor 208 via a communication path, a measured blood glucose level signal 212, which may be a second signal, indicating an approximate measured value of the actual blood glucose level of the user.

Based on the desired blood glucose level signal 210 and the measured actual blood glucose level signal 212, the controller 202 may generate one or more control signals 214 for directing operation of the pump 204. For example, one of the control signals 214 may cause the pump 204 to deliver a dose of insulin 216 to a user via output 206. The dose of insulin 216 may, for example, be determined based on a difference between the desired blood glucose level signal 210 and the actual blood glucose signal level 212. The cost function referenced above plays a role in determining the dosage as part of the closed loop control system as will be described below. The dose of insulin 216 may be determined as an appropriate amount of insulin to drive the actual blood glucose level of the user to the desired blood glucose level. Based on operation of the pump 204 as determined by the control signals 214, the user may receive the insulin 216 from the pump 204.

Figure 3:
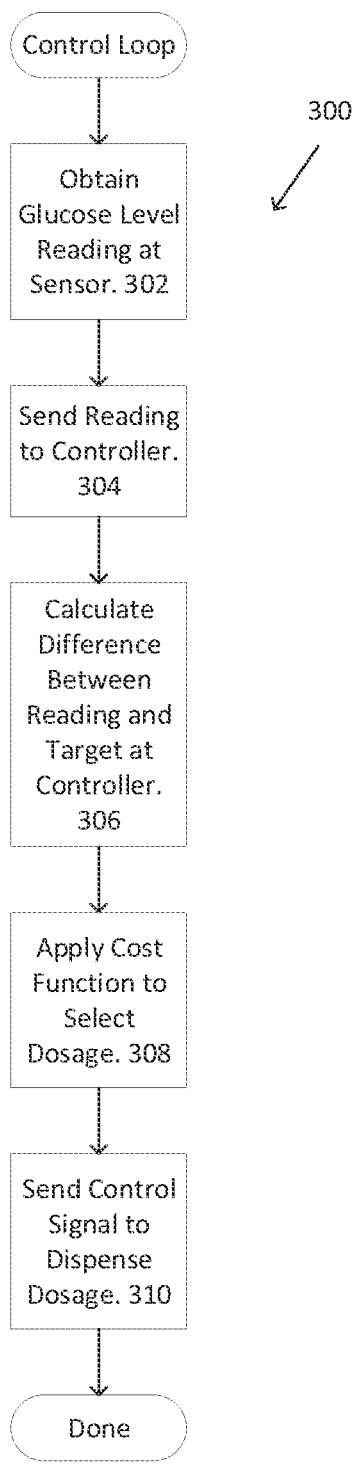
FIG. 3 depicts a flowchart of illustrative steps that may be performed by exemplary embodiments in determining what dose of insulin to deliver the user as part of the closed loop control system.

FIG. 3 depicts a flowchart 300 of steps that may be performed by exemplary embodiments of the AID system in determining what dose of insulin to deliver to the user as part of the closed loop control system. These steps may be performed by controller 110, processor 119 or other components (at least in part), like smartwatch 130, fitness monitor or wearable device 134. That said, for purposes of simplicity below, we will just refer to controller 110. Initially, as was described above relative to FIG. 2, a blood glucose level reading is obtained by the sensor 208 (302). The blood glucose level reading is sent via a signal 212 to the controller 202 (304). The controller 202 calculates an error value as the difference between the measured blood glucose level 212 and the desired BG level 210 (306). The closed loop control system attempts to minimize the aggregate penalty of the cost function over a wide range of possible dosages. The cost function is applied to the possible dosages, and the dosage with the best cost function value is selected (308). Depending on how the cost function is configured, the best value may be the lowest value or the highest value. The cost function used in exemplary embodiments will be described in more below. A control signal 214 may be generated by the controller 202 and sent to the pump 204 to cause the pump to deliver the desired insulin dose 216 to the user (310).

As discussed above, the exemplary embodiments may adjust the cost function to address persistent low-level blood glucose level excursions for users. As a starting point, it is helpful to review a typical conventional cost function. A typical formulation for cost J is:

$$J = Q \cdot \sum_{i=1}^{M} G_p(i)^2 + R \cdot \sum_{i=1}^{n} I_p(i)^2$$

where Q and R are weight coefficients as mentioned above, $G_p(i)^2$ is the square of the deviation between the projected blood glucose level for an insulin dosage at cycle i and the projected blood glucose level for the basal insulin dosage, M is the number of cycles in the prediction horizon, $I_p(i)^2$ is the square of the deviation between the projected insulin delivered at cycle i and the insulin for basal insulin delivery, and n is the control horizon in cycles. Thus, $Q \cdot \Sigma_{i=1}^{M} G_p(i)^2$ is the weighted glucose cost, and $R \cdot \Sigma_{i=1}^{n} I_p(i)^2$ is the weighted insulin cost. The total cost J is the sum of the weighted glucose cost and the weighted insulin cost. A cycle has a fixed interval, such 5 minutes.

The exemplary embodiments may modify the cost function to increasingly penalize blood glucose level excursions from the target blood glucose level by increasing basal insulin delivery over time. This may be done by reducing the insulin cost component in the cost function. Specifically, an $I_{out}$ variable may be introduced into the cost function formula to account for the additional insulin needed to reduce the low-level blood glucose level excursions. This additional insulin may be subtracted from insulin cost.

Figure 4:
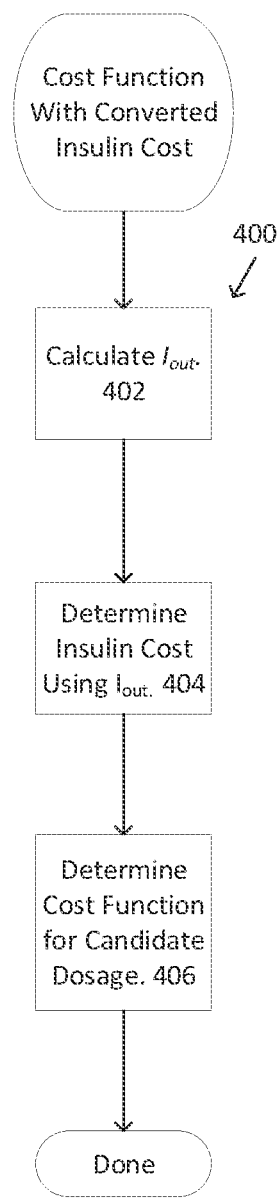
FIG. 4 depicts a flowchart of illustrative steps that may be performed to determine the cost of an insulin dosage with an adjusted cost function in exemplary embodiments.

FIG. 4 depicts a flowchart 400 of illustrative steps that may be performed to determine the cost of an insulin dosage with an adjusted cost function. The $I_{out}$ variable is calculated over the past h cycles. The cycles may be fixed length, such as 5 minutes per cycle. A suitable formula for calculating $I_{out}$ in an exemplary embodiment is:

$$I_{out} = K_i \sum_{i=1}^{h} \frac{G_h(t-i) - SP(t-i)}{\frac{CFrule}{TDI} \cdot \tau}$$

Where $G_h(t-i)$ is the blood glucose level at the ith cycle before cycle t, SP(t−i) is the target blood glucose level at the ith cycle before cycle t, CFrule is the correction factor for the user indicating how much 1 unit of insulin will lower the blood glucose level of the user over a period of time (like 2 to 4 hours), TDI is the total daily insulin for the user, τ is a parameter relating to the peak insulin action time for the user and $K_i$ is a tuning factor. Suitable example values for some of the variables are h to be 6 (i.e., 30 minutes), CFrule to be 1800 and τ to be 18 (i.e., 90 minutes or 18 5-minute cycles) with a range of 6 to 36.

The formula aggregates the blood glucose level excursions (see the numerator) over the last h cycles via the summation and determines the additional insulin requirements (see the conversion into insulin requirements in the denominator) required to bring the excursions to the target blood glucose level.

Referring again to FIG. 4, with $I_{out}$ calculated, the insulin cost for a proposed insulin dose being considered by the controller 110 as part of the AID approach may be determined at 404. A suitable cost function formula that is adaptive for cost $J_{new}$ is:

$$J_{new} = Q \cdot \Sigma_{i=1}^{M} G_p(i)^2 + R \cdot \Sigma_{i=1}^{n}(I_p(i) - I_{out})^2.$$

As can be seen, the difference in this cost function relative to the conventional cost function is that the insulin cost is calculated differently. The insulin cost subtracts out $I_{out}$. Thus, there is less of a penalty for additional insulin, and the basal dosage amount may increase to address the persistent low-level blood glucose level excursions.

With the insulin cost calculated as such, the weighted glucose cost may be determined and the cost function for the candidate dosage determined at 406.

In the above-described approach of exemplary embodiments, the controller 110 makes an adjustment to the insulin cost in the cost function to eliminate the low-level blood glucose level excursions as part of an AID control approach. Alternatively, the low-level blood glucose level excursions may be addressed by a separate mechanism that runs in conjunction with the un-modified AID control approach. A parallel controller may perform the operations described below to address the persistent low-level blood glucose level excursions.

Figure 5:
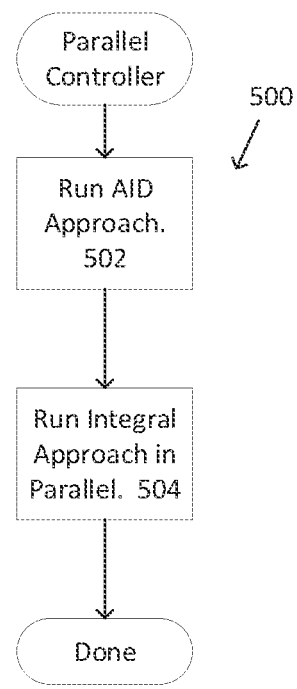
FIG. 5 depicts a flowchart of illustrative steps that may be performed when a parallel controller is provided to reduce low-level glucose excursions.

FIG. 5 depicts a flowchart 500 of illustrative steps for such exemplary embodiments. The AID approach is run as described above for conventional systems using a conventional cost function 502. The integral approach (labelled as such because it determines the integral of the insulin needed to reduce or eliminate the blood glucose level excursions) described below is run in parallel on a parallel controller 504. The parallel controller may be part of a single controller that performs the two control approaches in parallel or may run on separate controllers on a same drug delivery device or management device.

The controller running in parallel may make a request for an insulin dosage that is separate from that of the AID control approach of the other controller. The aim of the separate request is to provide additional insulin to eliminate or reduce the blood glucose level excursions. The parallel controller may determine the insulin amount requested $I_{integral}(t)$ as:

$$I_{integral}(t) = \max\left\{\min\left(\begin{array}{c}\dfrac{G_h(t) - SP(t)}{\dfrac{CFrule}{TDI}}, \\ K_i \sum_{i=1}^{h}(G_h(t-i) - SP(t-i))\end{array}\right), 0\right\}.$$

Figure 6:
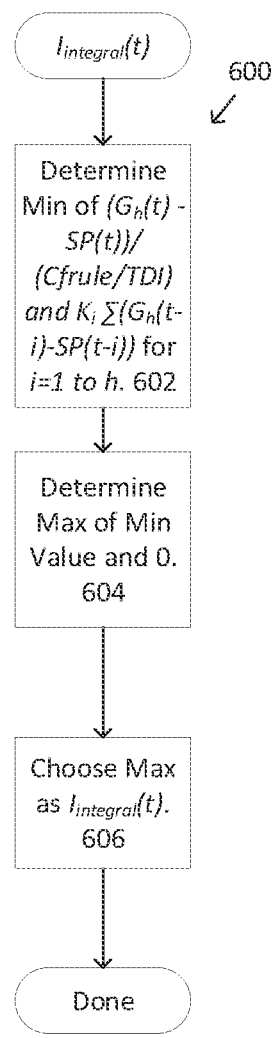
FIG. 6 depicts a flowchart of illustrative steps that may be performed to calculate $I_{out}$ in exemplary embodiments.

As shown in the flowchart of FIG. 6, the formula calculates the minimum of $$\dfrac{G_h(t) - SP(t)}{\dfrac{CFrule}{TDI}} \text{ and } K_i \sum_{i=1}^{h}(G_h(t-i) - SP(t-i)) \text{ at } 602.$$

The value $$\dfrac{G_h(t) - SP(t)}{\dfrac{CFrule}{TDI}}$$

is the amount of insulin needed to compensate for the excess blood glucose level at time t. The value $K_i \Sigma_{i=1}^{h}(G_h(t-i)-SP(t-i))$ is the cumulative difference in the blood glucose level relative to the target blood glucose level (i.e., the total glucose blood level excursions) over the past h cycles multiplied by a tuning factor $K_i$. In some embodiments, $K_i$ may be made dependent on the user's average insulin requirements, such as TDI. The insulin amount requested is bounded at 0, so the formula takes the maximum or the calculated values and zero. This ensures that the amount request is greater than or equal to zero at 604. The largest value is chosen as $I_{integral}(t)$ at 606.

In exemplary embodiments, the cost function may also be adjusted to modify the aggressiveness of the AID control approach based on an average time a user maintains his or her blood glucose level in an acceptable range. As was mentioned above, the current performance is measured relative to best performance to determine how aggressive to be in adapting the AID control approach. One way of achieving this adjustment in aggressiveness is to modify the R coefficient for insulin cost in the cost function. In exemplary embodiments, the cost function detailed above may be used. Thus, the cost function may be:

$$J = Q \cdot \sum_{i=1}^{M} G_p(i)^2 + R \cdot \sum_{i=1}^{n} I_p(i)^2$$

With $Q$ fixed at 1, so that R controls the aggressiveness of the adaptability of the AID control approach.

In some exemplary embodiments, R may be determined by the formula:

$$R = \left(1 - 0.2 \cdot \dfrac{h}{288}\right) \cdot R_{base} + 0.2 \cdot R_{base} \cdot \left(\dfrac{TIR_{h,70<CGM<180}}{TIR_{Max}}\right)^2$$

Where $R_{base}$ is a baseline tuning factor relating to the aggressiveness of the AID control approach, $TIR_{h,70<CGM<180}$ is the percentage of time that the blood glucose level was in the acceptable range between 70 and 180 mg/dL during the h cycles for which there is available blood glucose level history to the controller 110, 288 is the number of cycles per day with 5 minute cycles, and $TIR_{max}$ is the maximum percentage of time in range for the user over all of the available blood glucose level history.

Figure 7:
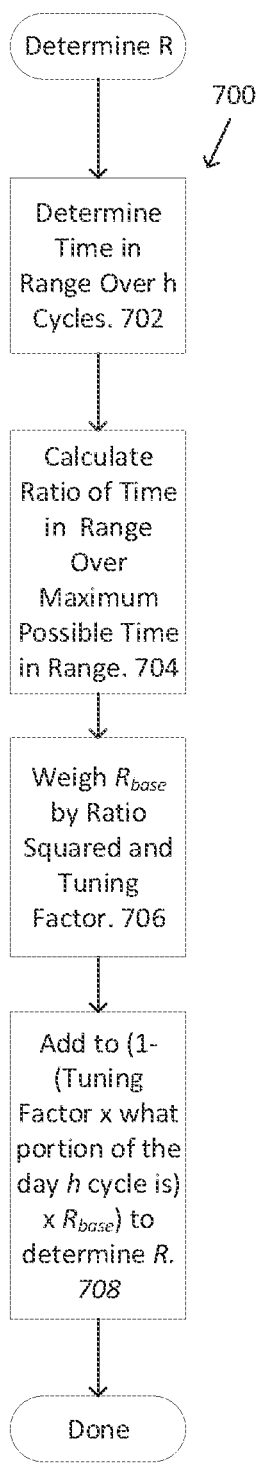
FIG. 7 depicts a flowchart of illustrative steps that may be performed in exemplary embodiments to determine the weight coefficient R.

FIG. 7 depicts a flowchart 700 of steps that may be performed in exemplary embodiments to determine R. The percentage of time in range over the h cycles of available blood glucose level history is determined at 702. The percentage of time in range is represented in the above formula for R by the variable $TIR_{h,70<CGM<180}$. It should be appreciated that other acceptable ranges that differ from the range between 70 and 180 mg/dL may be used in some embodiments. $TIR_{max}$ is determined as will be detailed below and the ratio $$\frac{TIR_{h,70<CGM<180}}{TIR_{Max}}$$

is determined at 704. This ratio represents the amount of time the blood glucose level of the user was in range versus a maximum available time in range. Hence, the ratio is a good estimate of how well the user manages his/her blood glucose level. A large ratio closer to 1 indicates that the user manages his/her blood glucose level well, where a small ratio indicates that the user does not manage his/her blood glucose level well. $R_{base}$ is weighted by the product of the ratio squared times a tuning factor (e.g., 0.2) at 706. Hence, R is larger and the adaptivity is more aggressive when the ratio is higher, and R is smaller and the adaptivity is less aggressive when the ratio is smaller. At 708, the weighted squared ratio is added to $$\left(1 - 0.2 \cdot \frac{h}{288}\right) \cdot R_{base}.$$

The variable h is the number of cycles of available blood glucose level history for the user. So, if there is more history, the ratio $$\frac{h}{288}$$

approaches one and the weighted squared ratio contributes more to R. This is because the confidence in the data grows as there is more data available.

Figure 8:
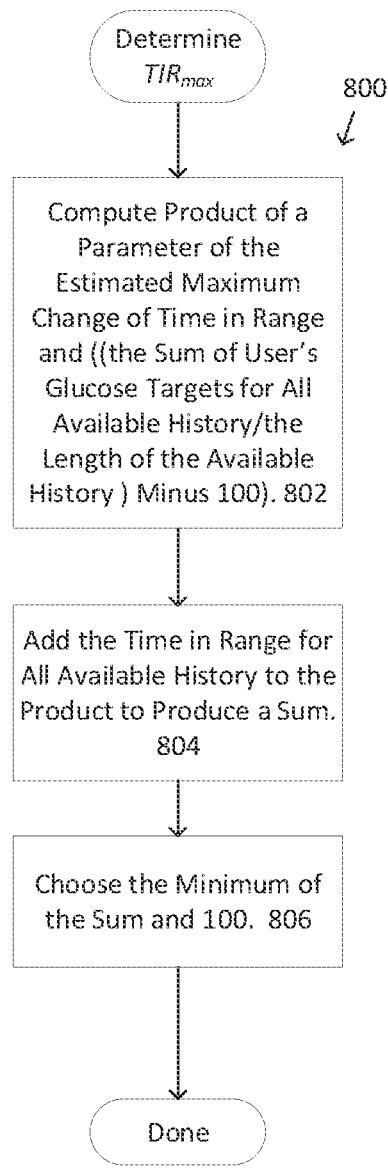
FIG. 8 depicts a flowchart of illustrative steps that may be performed to determine $TIR_{max}$ in exemplary embodiments.

FIG. 8 depicts a flowchart 800 of illustrative steps that may be performed to determine $TIR_{max}$. A formula for $TIR_{max}$ that may be used in exemplary embodiments is:

$$TIR_{Max} = \min\left(\begin{array}{c} 100, TIR_{all\ history,70<CGM<180} + \\ 0.3 \cdot \left(\frac{\sum_{k=1}^{L_{all\ history}} SP(i)}{L_{all\ history}} - 100\right) \end{array}\right)$$

where $TIR_{all\ history,70<CGM<180}$ is the percentage of time that the blood glucose level of the user was in the acceptable range over all of the available blood glucose level history for the user and $L_{all\ history}$ is the length of the all available blood glucose level history for the user.

The fraction $$\frac{\sum_{k=1}^{L_{all\ history}} SP(i)}{L_{all\ history}}$$

determines the user's average blood glucose level target over the available history. The value 100 is subtracted from this fraction and multiplied by a tuning factor (e.g., 0.3) at 802. The resulting value of the calculation made at 802 is added to the time in range over all of the available blood glucose level history at 804. The smaller of the sum of the calculation made at 804 and 100 is chosen as the maximum percentage in range at 806.

While the discussion has focused on exemplary embodiments herein, it should be appreciated that various changes in form and detail without departing from the intended scope as defined in the appended claims.

The invention claimed is:

1. A device for controlling insulin deliveries to a user by an insulin pump, comprising:
    a glucose sensor interface with a glucose sensor to obtain glucose readings for the user from the glucose sensor;
    an insulin pump interface for communicating with the insulin pump to control delivery of insulin to the user by the insulin pump;
    a processor configured to implement a control loop to control the delivery of insulin by the insulin pump, wherein the processor selects an insulin delivery dosage for a next delivery among delivery dosage options that has a best value of a cost function and wherein the cost function for each of the delivery dosage options:
        has a glucose cost component reflective of a difference between a glucose level that the delivery dosage option is predicted to produce for the user and a glucose level for the user relative to a projected glucose level with basal insulin delivery,
        has an insulin cost component reflective of a difference between a deviation of the delivery dosage option from a current basal insulin dosage and a converted amount of insulin needed to compensate for glucose excursions above a target for an interval of time, wherein the processor is configured to calculate the converted amount of insulin needed to compensate for glucose excursions above the target for the interval of time by determining a magnitude of the glucose excursions above the target for the interval,
        has a glucose cost weight coefficient for weighting the glucose cost component, and
        has an insulin cost weight coefficient for weighting the insulin cost component.

2. The device for controlling insulin deliveries of claim 1, wherein the device for controlling insulin deliveries is a drug delivery device that includes the insulin pump.

3. The device for controlling insulin deliveries of claim 1, wherein the device for controlling insulin deliveries is a management device for the insulin pump that does not include the insulin pump.

4. The device for controlling insulin deliveries of claim 1, wherein the processor is configured to determine the magnitude of the glucose excursions above the target for the interval of time by summing glucose excursions above a target of blood glucose level for each cycle in the interval.

5. The device for controlling insulin deliveries of claim 4, wherein the processor is configured for determining the converted amount of insulin needed to compensate for glucose excursions above the target for the interval of time by applying a conversion factor to the determined magnitude of the glucose excursions above the target.

6. A device for controlling insulin deliveries to a user from by an insulin pump, comprising:
    a glucose sensor interface with a glucose sensor to obtain glucose readings for the user from the glucose sensor;
    an insulin pump interface for communicating with the insulin pump to control delivery of insulin to the user by the insulin pump; and one or more processors configured to implement a control loop to control the delivery of insulin by the insulin pump such that the processor selects an insulin delivery dosage for a next delivery among delivery dosage options that has a best value of a cost function and also configured to implement a parallel integral control approach that requests an additional insulin dosage from the insulin pump to eliminate positive glucose excursions that are not eliminated by the control loop and that does not request insulin when there are not positive glucose excursions to be eliminated.

7. The device for controlling insulin deliveries of claim 6, wherein the device for controlling insulin deliveries is one of an insulin delivery device or a management device for the for controlling insulin delivery device.

8. The device for controlling insulin deliveries of claim 7, wherein the one or more processors are configured so that the parallel integral approach determines an amount of insulin needed to eliminate a current magnitude of a positive glucose excursion.

9. The device for controlling insulin deliveries of claim 8, wherein the one or more processors are configured so that the parallel integral approach determines an aggregate magnitude of glucose excursions for a past number of cycles.

10. The device for controlling insulin deliveries of claim 9, wherein the one or more processors are configured so that the parallel integral approach determines a product of the aggregate magnitude of glucose excursions for a past number of cycles and a tuning factor.

11. The device for controlling insulin deliveries of claim 10, wherein the one or more processors are configured so that the parallel integral approach selects either the amount of insulin needed to eliminate a current magnitude of a positive glucose excursion or the product as the additional insulin dosage.

12. A device for controlling insulin deliveries to a user by an insulin pump, comprising:
a glucose sensor interface with a glucose sensor to obtain glucose readings for the user from the glucose sensor;
an insulin pump interface for communicating with the insulin pump to control delivery of insulin to the user by the insulin pump;
a processor configured to implement a control loop to control the delivery of insulin by the insulin pump, wherein the processor selects an insulin delivery dosage for a next delivery among the delivery dosage options that has a best value of a cost function and wherein the cost function for each of the delivery dosage options:
has a glucose cost component reflective of a difference between a glucose level that the delivery dosage option is predicted to produce for the user and a target glucose level for the user,
has an insulin cost component reflective of a deviation of the delivery dosage option from a current basal insulin dosage,
has a glucose cost weight coefficient for weighting the glucose cost component, and
has an insulin cost weight coefficient for weighting the insulin cost component, wherein the insulin cost weight coefficient is based on a ratio of time in a desired range for glucose values of the user and maximum time in the desired range from a history of glucose values for the user and wherein the insulin cost weight coefficient increases in value as the ratio of time in a desired range for glucose values of the user and maximum time in the desired range from a history of glucose values for the user increases.

13. The device for controlling insulin deliveries of claim 12, wherein the insulin cost weight coefficient is also based on a base value for the insulin cost weight coefficient.

14. The device for controlling insulin deliveries of claim 12, wherein the maximum time in the desired range is a percentage value.

15. The device for controlling insulin deliveries of claim 12, wherein the processor is configured to determine the maximum time in the desired range based on an average target blood glucose value of the user over the history of glucose values for the user.

16. The device for controlling insulin deliveries of claim 15, wherein the processor is configured to determine the maximum time in the desired range based additionally on a percentage of time that glucose values for the user were in range over the history of glucose values for the user.

17. The device for controlling insulin deliveries of claim 12, wherein the device for controlling insulin deliveries is one of an insulin delivery device or a management device for an insulin delivery device.

* * * * *